US009521956B2

(12) United States Patent
Bedingham et al.

(10) Patent No.: US 9,521,956 B2
(45) Date of Patent: Dec. 20, 2016

(54) ENHANCED AUSCULTATORY SENSOR AND ANALYSIS FOR PATIENT DIAGNOSIS

(71) Applicant: 3M INNOVATIVE PROPERTIES COMPANY, St. Paul, MN (US)

(72) Inventors: William Bedingham, Woodbury, MN (US); Thomas P. Schmidt, Blaine, MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 14/405,861

(22) PCT Filed: May 15, 2013

(86) PCT No.: PCT/US2013/041167

§ 371 (c)(1),
(2) Date: Dec. 5, 2014

(87) PCT Pub. No.: WO2013/184315

PCT Pub. Date: Dec. 12, 2013

(65) Prior Publication Data

US 2015/0164340 A1 Jun. 18, 2015

Related U.S. Application Data

(60) Provisional application No. 61/655,710, filed on Jun. 5, 2012, provisional application No. 61/781,189, filed on Mar. 14, 2013.

(51) Int. Cl.
*A61B 5/04* (2006.01)
*A61B 5/0205* (2006.01)
(Continued)

(52) U.S. Cl.
CPC ........... *A61B 5/0205* (2013.01); *A61B 5/0006* (2013.01); *A61B 5/0402* (2013.01);
(Continued)

(58) Field of Classification Search
USPC ........................................................ 600/528
See application file for complete search history.

(56) References Cited

U.S. PATENT DOCUMENTS 4,362,164 A 12/1982 Little
4,428,380 A 1/1984 Wong
(Continued)

FOREIGN PATENT DOCUMENTS

CN 2754560 2/2006
JP 2012-055354 3/2012
(Continued)

OTHER PUBLICATIONS

International Search Report for PCT International Application No. PCT/US2013/041167, mailed on Sep. 26, 2013, 4pgs.

*Primary Examiner* — Nicole F Johnson

(57) ABSTRACT

In general, techniques and systems for detecting acoustic signals and generating phonocardiograms are described. In one example, a system may include an acoustic sensor configured to detect an acoustic signal from a heart of a patient. The system may also include a sensing module configured to detect an electrical signal from the heart of the patient via two or more electrodes and at least one processor configured to generate a composite phonocardiogram based the acoustic signal and the electrical signal detected over a plurality of cardiac cycles of the heart, wherein the composite phonocardiogram is generated for a representative cardiac cycle. The system may be provided in a single device or multiple devices configured to transmit information between the devices.

13 Claims, 30 Drawing Sheets

(51) Int. Cl.

| | |
|---|---|
| ***A61B 7/04*** | (2006.01) |
| ***A61B 5/0402*** | (2006.01) |
| ***A61B 5/00*** | (2006.01) |
| ***A61B 5/0408*** | (2006.01) |
| ***A61B 5/0456*** | (2006.01) |
| *A61B 5/08* | (2006.01) |

(52) U.S. Cl.

CPC ........ *A61B 5/04014* (2013.01); *A61B 5/0456* (2013.01); *A61B 5/04085* (2013.01); *A61B 5/742* (2013.01); *A61B 5/7405* (2013.01); *A61B 5/7475* (2013.01); *A61B 7/04* (2013.01); *A61B 7/045* (2013.01); *A61B 5/0816* (2013.01)

(56) References Cited

U.S. PATENT DOCUMENTS

| | | | |
|---|---|---|---|
| 4,628,939 | A | 12/1986 | Little |
| 4,905,706 | A | 3/1990 | Duff |
| 5,025,809 | A | 6/1991 | Johnson |
| 5,337,752 | A | 8/1994 | Reeves |
| 6,134,331 | A | 10/2000 | Baekgaard |
| 6,520,924 | B2 | 2/2003 | Lee |
| 6,544,189 | B2 | 4/2003 | Watrous |
| 6,572,560 | B1 | 6/2003 | Watrous |
| 6,629,937 | B2 | 10/2003 | Watrous |
| 6,643,548 | B1 | 11/2003 | Mai |
| 6,658,292 | B2 | 12/2003 | Kroll |
| 6,869,404 | B2 | 3/2005 | Schulhauser |
| 6,878,117 | B1 | 4/2005 | Watrous |
| 6,953,436 | B2 | 10/2005 | Watrous |
| 6,999,592 | B2 | 2/2006 | Chelen |
| 7,074,195 | B2 | 7/2006 | Nelson |
| 7,096,060 | B2 | 8/2006 | Arand |
| 7,110,804 | B2 | 9/2006 | Baumer |
| 7,130,429 | B1 | 10/2006 | Dalgaard |
| 7,174,203 | B2 | 2/2007 | Arand |
| 7,300,406 | B2 | 11/2007 | Carter |
| 7,300,407 | B2 | 11/2007 | Watrous |
| 7,302,290 | B2 | 11/2007 | Bauer |
| 7,346,174 | B1 | 3/2008 | Smith |
| D566,847 | S | 4/2008 | Baumer |
| 7,471,290 | B2 | 12/2008 | Wang |
| 7,668,589 | B2 | 2/2010 | Bauer |
| 7,736,319 | B2 | 6/2010 | Patangay |
| 2006/0135876 | A1 | 6/2006 | Andresen |
| 2006/0293714 | A1* | 12/2006 | Salo .................. A61M 5/14276 607/9 |
| 2008/0046015 | A1 | 2/2008 | Freeman |
| 2008/0071184 | A1 | 3/2008 | Carter |
| 2008/0273709 | A1* | 11/2008 | Thiagarajan ........... A61B 7/005 381/67 |
| 2011/0098587 | A1 | 4/2011 | Haefner |
| 2011/0137210 | A1 | 6/2011 | Johnson |
| 2012/0071767 | A1 | 3/2012 | Popov |

FOREIGN PATENT DOCUMENTS

| | | |
|---|---|---|
| JP | 2012-075936 | 4/2012 |
| WO | WO 02-09396 | 1/2002 |

* cited by examiner

ENHANCED AUSCULTATORY SENSOR AND ANALYSIS FOR PATIENT DIAGNOSIS

BACKGROUND

A variety of devices have been developed to detect sounds produced by the body, such as heart and lung sounds. These devices range from primarily mechanical devices, such as a stethoscope, to various electronic devices, such as microphones and transducers. The stethoscope, for example, is a fundamental tool used in the diagnosis of diseases and conditions of the cardiovascular system. It serves as the most commonly employed technique for diagnosis of such diseases and conditions in primary health care and in circumstances where sophisticated medical equipment is not available, such as remote areas.

Clinicians readily appreciate that detecting relevant cardiac symptoms and forming a diagnosis based on sounds heard through the stethoscope, for example, is a skill that can take years to acquire and refine. Heart sounds are often separated from one another by relatively short periods of time, and abnormal sounds that may be characteristic of cardiac disorders may be less audible than normal heart sounds. In some examples, a system may be used to generate a graphical representation (e.g., a phonocardiogram) of detected heart sounds.

SUMMARY

This disclosure is generally directed to techniques, devices, and systems for detecting acoustic signals from a patient and generating a phonocardiogram for diagnosing one or more conditions of the patient. For example, a detection device is described that includes an acoustic sensor that detects acoustic signals from a heart of the patient. The detection device may also be coupled to two or more electrodes that detect electrical signals of the heart. The detected electrical signals (e.g., an r-wave of an electrocardiogram) may be used to synchronize acoustic signals (e.g., S1 and S2 heart sounds) from multiple cardiac cycles to reinforce the heart sounds and produce a composite phonocardiogram (PCG). The composite PCG may be presented to a user by generating an audible signal of the composite PCG and/or generating a visual display of the composite PCG.

In one example, a system includes an acoustic sensor configured to detect an acoustic signal from a heart of a patient, a sensing module configured to detect an electrical signal from the heart of the patient via two or more electrodes, and at least one processor configured to generate a composite phonocardiogram based on the acoustic signal and the electrical signal detected over at least a plurality of cardiac cycles of the heart, wherein the composite phonocardiogram is generated for a representative cardiac cycle.

In another example, a method includes detecting an acoustic signal from a heart of a patient, detecting an electrical signal from the heart of the patient via two or more electrodes, for each cardiac cycle of a plurality of cardiac cycles, identifying a trigger point associated with an r-wave of each cardiac cycle of the detected electrical signal, generating acoustic information from the detected acoustic signal, synchronizing the acoustic information to the trigger point for each cardiac cycle, and generating a composite phonocardiogram for a composite cardiac cycle based on the synchronized acoustic information.

In another example, a device includes a housing, an acoustic sensor configured to detect an acoustic signal from a heart of a patient, at least three electrodes disposed on at least one external surface of the housing, a sensing module within the housing, electrically coupled to the at least three electrodes, and configured to detect an electrical signal from the heart of the patient via the at least three electrodes, and at least one processor within the housing and configured to generate a phonocardiogram based the acoustic signal and the electrical signal detected over at least one cardiac cycle of the heart.

In another example, a device includes a housing, two or more acoustic sensors each configured to detect a respective acoustic signal from a heart of a patient, at least one processor within the housing and configured to determine a quality of the respective acoustic signals and, based on the quality of the respective acoustic signals, identify a direction in which the housing is to be moved to increase an overall quality of a composite acoustic signal generated by the two or more acoustic sensors, and a user interface configured to present the direction to a user.

In another example, a system includes an acoustic sensor configured to detect an acoustic signal from a heart of a patient over a plurality of cardiac cycles, a sensing module configured to detect an electrical signal from the heart of the patient via two or more electrodes over the plurality of cardiac cycles, at least one processor configured to generate a composite phonocardiogram by synchronizing a plurality of portions of the acoustic signal based on one or more triggers determined from the electrical signal, each of the portions associated with one of the cardiac cycles, and a sound generation device configured to present the composite phonocardiogram audibly to a user.

In another example, a system includes a processor configured to generate a waveform based on an acoustic signal and an electrical signal detected over at least one cardiac cycle of the heart, generate a phonocardiogram by mirroring the waveform about an axis of the waveform, and identify at least one heart sound within the phonocardiogram, and a user interface configured to visually present the phonocardiogram and the identification.

The details of one or more examples are set forth in the accompanying drawings and the description below. Other features, objects, and advantages will be apparent from the description and drawings, and from the claims.

DETAILED DESCRIPTION

Figure 1:
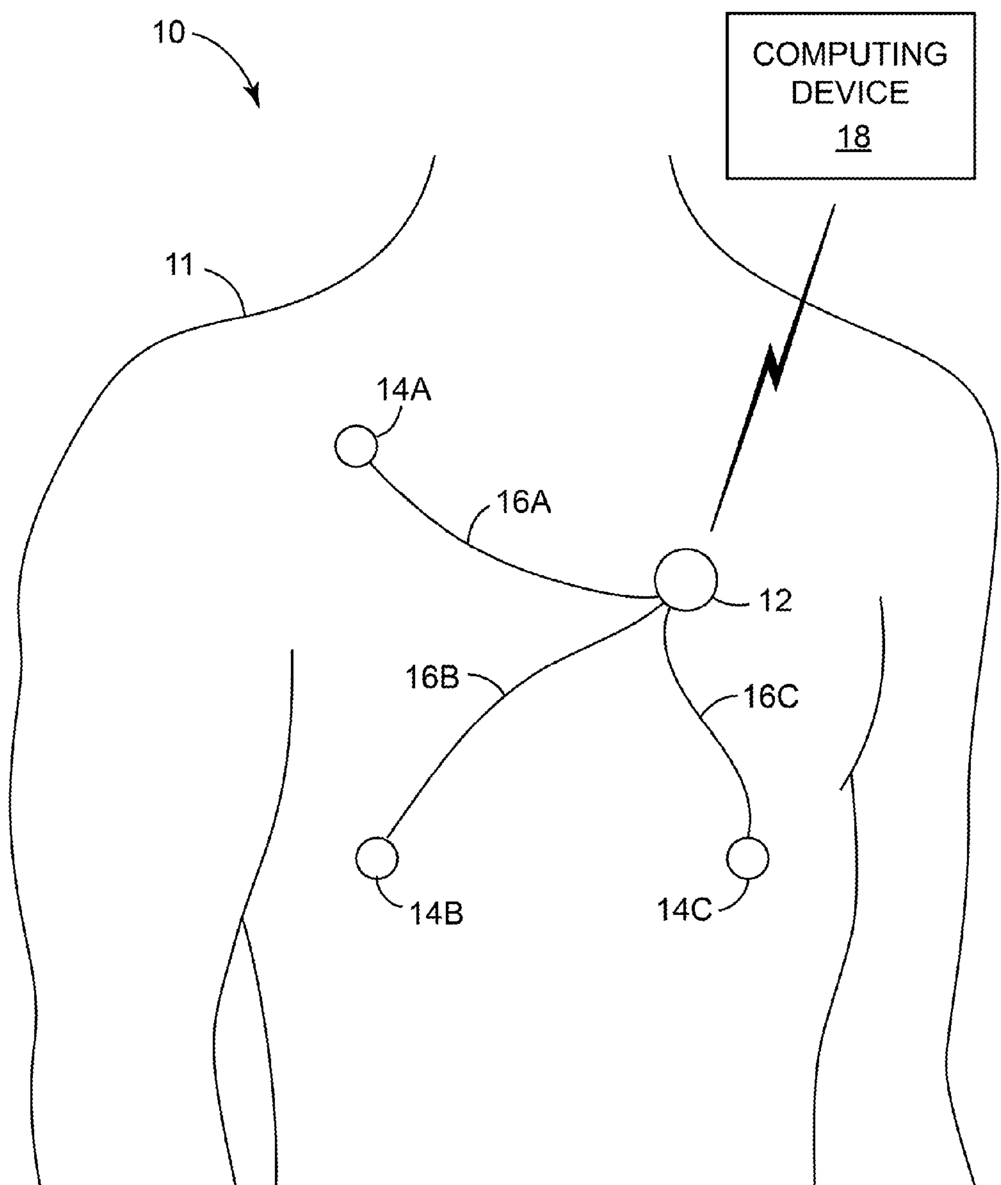
FIG. 1 is a conceptual diagram illustrating an example detection device coupled to multiple electrodes and configured to communicate with a computing device, in accordance with one or more aspects of the present disclosure.

In general, this disclosure is directed to techniques, devices, and systems for detecting acoustic signals from a patient and generating a composite phonocardiogram (PCG) for diagnosing one or more conditions of the patient. Cardiac auscultation is a technique in which a clinician may listen to the sounds made by the heart with a stethoscope or other listening instrument. During each cardiac cycle, blood enters and exits the chambers of the heart through respective valves. Normal cardiac function may change over time due to one or more diseases or traumatic events. For example, a valve may begin to malfunction, a blood vessel may harden, a blood vessel may develop plaque that restricts blood flow, or cardiac muscle function may diminish. Any change to cardiac function may result in a change to the sounds produced during each cardiac cycle. These different sounds may be referred to as heart sound pathologies.

Cardiac auscultation may be an effective and inexpensive tool for diagnosing a variety of different diseases within a patient. However, identifying abnormal sounds using cardiac auscultation can be a difficult skill to master. Within a brief examination period on the order of minutes, the clinician must recognize when one of over fifty different pathologies is present among the normal cardiac sounds (e.g., a typical "lub dub" sound) during an approximately one second pattern (e.g., the cardiac cycle). Therefore, effective cardiac auscultation may require extensive training, years of experience, and frequent repetition to retain the skill. Without effective use of cardiac auscultation to diagnose a patient, the clinician may resort to more extensive and expensive diagnostic and/or imaging techniques to treat the patient.

Techniques of this disclosure may, in various instances, facilitate the use of PCGs for the diagnosis of cardiac pathologies detectable from heart sound variations. The system may include a detection device that includes an acoustic sensor. The detection device may be an external device that is placed on an external surface of the skin of the patient. The acoustic sensor may detect acoustic signals from a heart of the patient. The detection device may also be coupled to two or more electrodes that detect electrical signals of the heart. In one example, the detection device may be coupled to each of the electrodes via a respective wire. In another example, the detection device may carry each of the electrodes on the housing of the detection device. The detection device may transmit detected and/or generated information to a computing device (e.g., a notebook computer, tablet computer, mobile phone, or any other computing device) via direct wireless communication or over a network.

The detected electrical signals (e.g., an R-wave and/or T-wave of an electrocardiogram) may be used to synchronize acoustic signals (e.g., S1 and S2 heart sounds) from multiple cardiac cycles to reinforce the heart sounds. For example, the system may detect an r-wave and use the r-wave detection as a trigger for synchronizing the acoustic signals from each cardiac cycle. To reinforce the heart sounds, acoustic signals from each of multiple cardiac cycles may be averaged or summed to produce a composite phonocardiogram (PCG). This averaging may reduce the presence of noise in the composite PCG that may otherwise be present in the acoustic signals for individual cardiac cycles. The composite PCG may represent the heart sounds during one cardiac cycle of the patient. Although acoustic signals may be synchronized using an electrogram, acoustic signals may instead be synchronized based on respiration features and/or detected motion or position of the patient. One or more triggers from an electrogram, respiration, and/or detected motion or position may be used individually or in combination to synchronize the acoustic signals for a composite PCG.

Although the composite PCG may be generated using consecutive cardiac cycles, the acoustic signals from multiple cardiac cycles may be separated according to one or more criteria. For example, the system may generate a separate composite PCG for each phase of patient breathing. The r-wave from the electrocardiogram (e.g., the electrical signals), may vary in amplitude at different phases of patient breathing. For example, the amplitude of r-waves may increase during inspiration and decrease during expiration. The system may then group or sort acoustic signals from cardiac cycles according to the cardiac cycle timing during the breathing process. For each breathing phase, the system may average or sum the grouped acoustic signals to generate the composite PCG. Since certain heart sound pathologies may be more prevalent in one breathing phase than another breathing phase, separate composite PCGs may facilitate identification of a pathology and patient diagnosis.

In another example, the system may generate separate composite PCGs for different activities of the patient during which the acoustic signals were detected. For example, different composite PCGs may be generated for when the patient is bending over, standing up, lying down, or performing any other activity or maneuver. Each composite PCG may be generated by averaging only the acoustic signals detected for cardiac cycles that occurred during each activity. In other words, an output from an accelerometer or other activity sensor may be used to group the acoustic signals.

The composite PCG may be presented to a user by generating an audible signal of the composite PCG and/or generating a visual display of the composite PCG. For example, the detection device may transmit detected electrical signals and acoustic signals to a computing device (e.g., a notebook computer, a tablet computer, or a mobile phone) for processing and generating the composite PCG. A user interface of the computing device may then present a graph of the composite PCG. In some examples, the user interface may color code or otherwise identify abnormal sounds and/or normal sounds within the composite PCG. In other examples, the user interface may include a speaker that generates an audible representation of the composite PCG. In this manner, the audible representation of the composite PCG may be played to the user alone or on top of (or overlaid with) real-time acoustic signals presented audibly to the user. In other examples, the detection device may send an audio signal to a wireless headset, a wired headset, or an electronic stethoscope. A user may then listen to the audio signal and/or composite PCGs using one of these devices. The audible and/or visual composite PCGs may enable a clinician to identify heart sound pathologies, diagnose a patient, and/or learn how to identify different heart sound pathologies. In some examples, the composite PCG may expose audible events otherwise covered or masked by noise or other heart sounds.

FIG. 1 is a conceptual diagram illustrating an example detection device 12 coupled to multiple electrodes 14A, 14B, and 14B (collectively "electrodes 14") and configured to communicate with computing device 18. As shown in FIG. 1, system 10 may include detection device 12, electrodes 14, and computing device 18. Each of electrodes 14 may be coupled to detection device 12 via a respective wire 16A, 16B, and 16C. Detection device 12 may include at least one acoustic sensor (not shown) that is configured to detect acoustic signals (e.g., sounds) from the heart of patient 11. System 10 may be used to perform any of the techniques or process described herein, such as generating and presenting a composite PCG to facilitate diagnosis of patient 11.

The acoustic sensor may be disposed within a housing of detection device 12 and/or on an external surface of the housing. A user (e.g., a clinician or patient 11) may place detection device 12 against the skin of the chest of patient 11 such that the acoustic sensor may physically contact the skin. Detection device 12 may be positioned over an intercostal space selected by the user. Acoustic signals generated by the heart and associated vasculature may then be detected by the acoustic sensor through the skin. In other examples, the acoustic sensor of detection device 12 may detect acoustic signals through fabric or another medium disposed between the acoustic sensor and the skin of patient 11.

System 10 may generate a composite PCG based on the detected acoustic signals from patient 12. As described herein, a composite PCG may be generated by averaging or summing the acoustic signals from multiple cardiac cycles. The averaged acoustic signals of each composite PCG may minimize or reduce noise and extraneous acoustic information present in each of the cardiac signals. Therefore, the composite PCG may be a representative cardiac cycle of the actual heart sounds produced by the heart on a consistent, beat-to-beat, basis. In some examples, detection device 12 may generate the composite PCG and transmit the composite PCG to computing device 18. In other examples, detection device 12 may transmit the detected acoustic signals as acoustic information to computing device 18. Computing device 18 may then process the acoustic signals and generate the composite PCG.

In some examples, the composite PCG may also reinforce subliminal sounds (e.g., sounds that may not be audible or discernible to the human ear due to low intensity and/or interfering noise). Example subliminal sounds may include S3 heart sounds, S4 heart sounds, or other abnormal sounds from the patient. System 10 may present the composite PCG visually as a waveform that includes the reinforced (e.g., amplified or non-amplified) subliminal sound envelope. System 10 may be configured to play back the audible composite PCG to the user with the previous subliminal or inaudible signal that is enhanced by reinforcement, noise reduction, and/or amplification.

The acoustic signals of each cardiac signal may be synchronized to correctly identify repetitive heart sounds of the acoustic signals. System 10 may utilize R-waves, for example, of detected electrical signals from the heart (e.g., an electrocardiogram) as a trigger to synchronize the acoustic signals. The electrical signals may be sensed by sensing vectors between two of electrodes 14. The sensed signals may be detected by detection device 12 once transmitted via wires 16. Detection device 12 may analyze the detected electrical signals and identify each R-wave of the cardiac signals within the electrical signals. The timing of each R-wave may then be used to synchronize the acoustic signals from the respective cardiac signals and generate the composite PCG. In some examples, detection device 12 may transmit the detected electrical signals to computing device 18 for analysis and to identify each R-wave as a trigger for the acoustic signals. Computing device 18 may then synchronize the acoustic signals needed for generating the composite PCG.

Detection device 12 may wirelessly communicate with computing device 18 or communicate with a physical connection in other examples. Computing device 18 may include a user interface for presenting information to the user, such as a visual or audible representation of the composite PCG. The user interface may include a display and/or a speaker. The user interface may include one or more input devices and/or output devices so that the user can communicate with computing device 18. In one example, the user interface may be a touch screen interface. In other examples, the user interface may include a display and one or more buttons, pads, joysticks, mice, tactile device, or any other device capable of turning user actions into electrical signals that control computing device 18. In any example, the user may interact with the user interface to provide input prior to or during the processes described herein. In some examples, computing device 18 may at least partially command detection device 12. In other examples, detection device 12 may at least partially command computing device 18.

System 10 may operate in real-time (e.g., generate composite PCG and present the composite PCG as the acoustic signals are detected) or store data for later review. For example, detection device 12 may record electrical signals and acoustic signals during a patient session. Detection device 12 may later transmit the recorded signals to computing device 18 via wired or wireless communication. Computing device 18 may then process the recorded signals and generate the composite PCG for review. Alternatively, detection device 12 may generate the composite PCG during or after the patient session and store the composite PCG for later transmission to computing device 18.

Detection device 12 may also include an adhesive patch on the surface that contacts the skin of patient 11. Alternatively, the detection device 12 may be secured to the patient 11 via an adhesive tape overlay, gauze, or other implements to secure detection device 12 to the patient 11 for the desired duration of signal acquisition. In some examples, detection device 12 may be reusable between different patients after replacing the adhesive patch and disinfecting detection device 12. In other examples, detection device 12 may be disposable after short-term or long-term single patient use. By adhering or otherwise securing detection device 12 to the patient 11, the acoustic and/or electric signals may be acquired over an extended period without requiring repeated physical interaction between a medical professional and the patient 11. For example, the desired signals may be acquired over a period of 90 seconds. In another example, the desired signals may be acquired over a period of hours, days, or even longer durations. In certain implementations, the extended acquisition period can produce a stronger composite signal, as discussed below.

Figure 2:
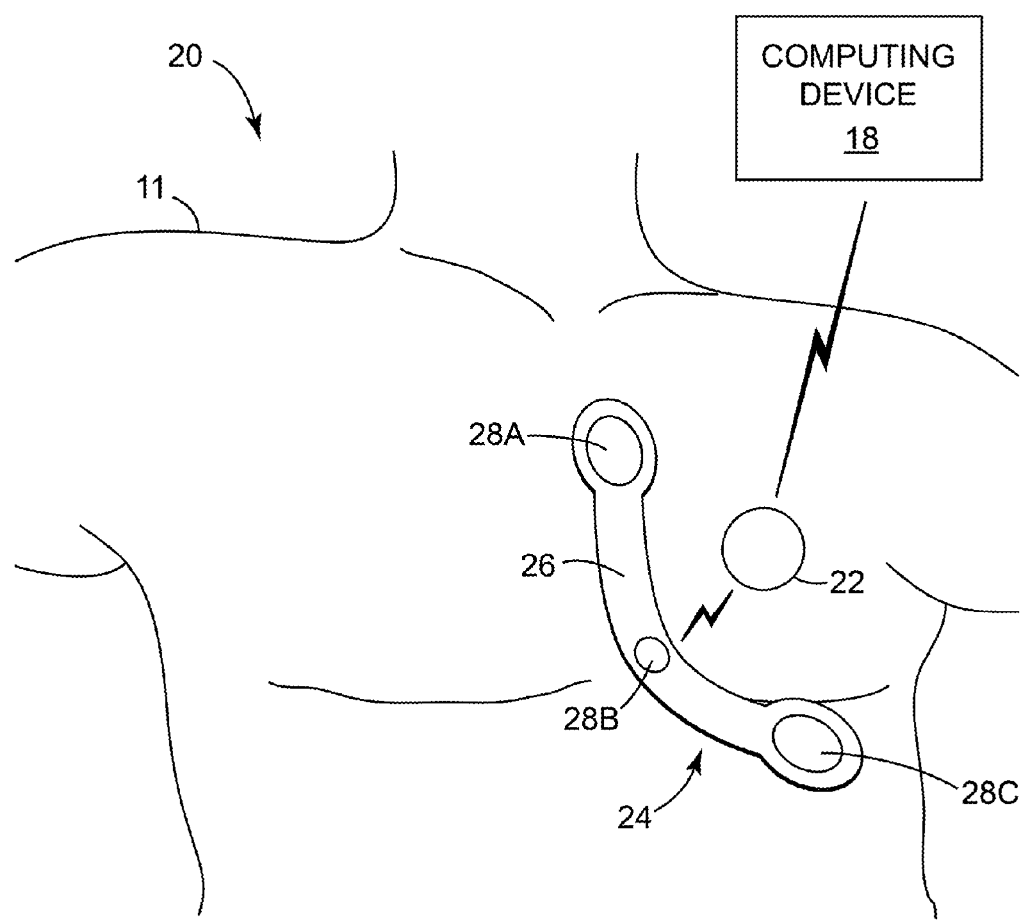
FIG. 2 is a conceptual diagram illustrating an example detection device configured to communicate with an electrode array and a computing device, in accordance with one or more aspects of the present disclosure.

FIG. 2 is a conceptual diagram illustrating an example system 20 that may include detection device 22 configured to communicate with electrode array 24 and computing device 18. System 20 may be substantially similar to system 10 of FIG. 1. However, system 20 may include electrode array 24 instead of individual electrodes 14. Housing 26 may include electrodes 28A, 28B, and 28C (collectively "electrodes 28"). Housing 26 may be constructed of a shape that retains each of electrodes 28 at a desired location with respect to the heart and other anatomical structures of patient 11. For example, housing 26 may take the shape of an "L" as shown in FIG. 2. Electrode array 24 may be positioned for desired vectors to detect the electrical signals with electrodes 28.

Housing 26 may be constructed of a flexible polymer or other material that facilitates contact of electrodes 28 with the skin of patient 11. Electrode array 24 may also include a telemetry module that communicates electrical signals sensed by electrodes 28 to detection device 22, either wirelessly or through a wired connection. Alternatively, detection device 22 may be electrically coupled to electrode array 24 via one or more cables or wires. Detection device 22 may also wirelessly communicate with computing device 18. Electrode array 24 may be disposable after each patient use or reusable between patients.

Figure 3:
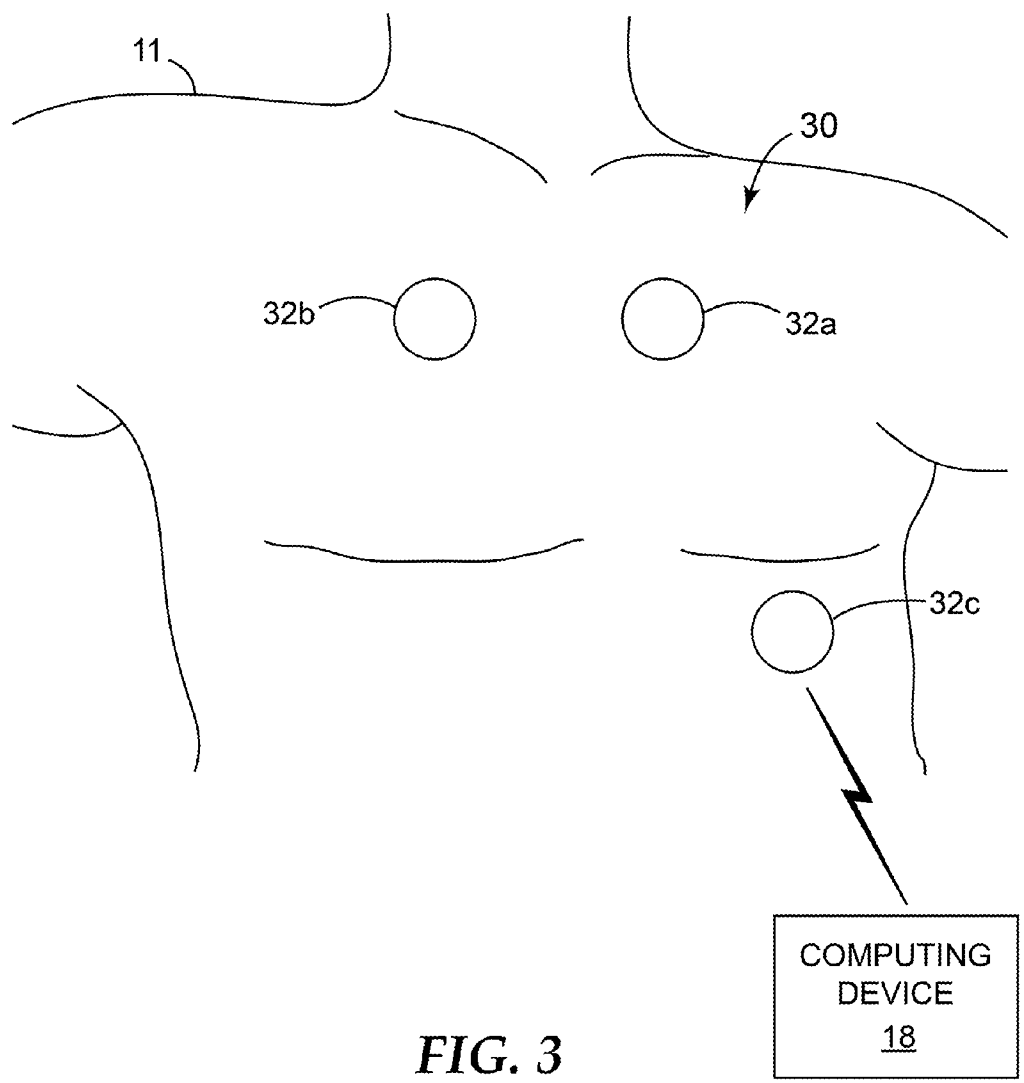
FIG. 3 is a conceptual diagram illustrating one or more detection devices carrying an acoustic sensor and multiple electrodes and configured to communicate with a computing device, in accordance with one or more aspects of the present disclosure.

FIG. 3 is a conceptual diagram illustrating example system 30 that includes a plurality of detection devices 32*a*, 32*b* and 32*c* and computing device 18. System 30 may be substantially similar to system 10 of FIG. 1. However, detection devices 32*a*, 32*b* and 32*c* of FIG. 3 may carry an acoustic sensor and multiple electrodes. For example, each of detection device 32*a*, 32*b* and 32*c* may have a housing that at least partially houses the acoustic sensor and the multiple electrodes (not shown). For example, each of the electrodes may be disposed on an external surface of the housing of each detection device 32*a*, 32*b* and 32*c* such that each electrode may be placed in electrical contact with patient 11. Detection devices 32*a*, 32*b* and 32*c* may also be configured to communicate with computing device 18. In other examples, each of detection devices 32*a*, 32*b* and 32*c* may also include processing circuitry and a user interface such that computing device 18 is not required to present a composite PCG to the user. Although FIG. 3 depicts system 30 as including three detection devices, system 30 may include any number of detection devices without departing from the intended scope of the present invention.

As shown in FIG. 3, in one embodiment, system 30 may have two separate detection devices 32*a* and 32*b* that have heart sound sensors/electrodes that are located on either side of the heart (e.g. 2L and Apex). The two sensor system provides enhanced sound localization and improves ECG feature identification. Additional sensors may also be added to provide further signal enhancements. The additional sensors can be automatically and intelligently added (i.e. scalable) and form a functional piconet (i.e. self-assembling network) that synchronizes and coordinates the data acquisition, analysis, and display.

The placement of the additional sensors can be guided by computing device 18 using an auscultation signal quality reporting system or an automated testing system, both of which are described below. For example, after a preliminary screen and analysis, computing device 18 can guide the clinician or patient to place additional sensors at prescribed locations, or to relocate the original sensor(s). The patient may also be instructed to perform additional physical maneuvers to enhance different features in the heart sound.

Figure 5:
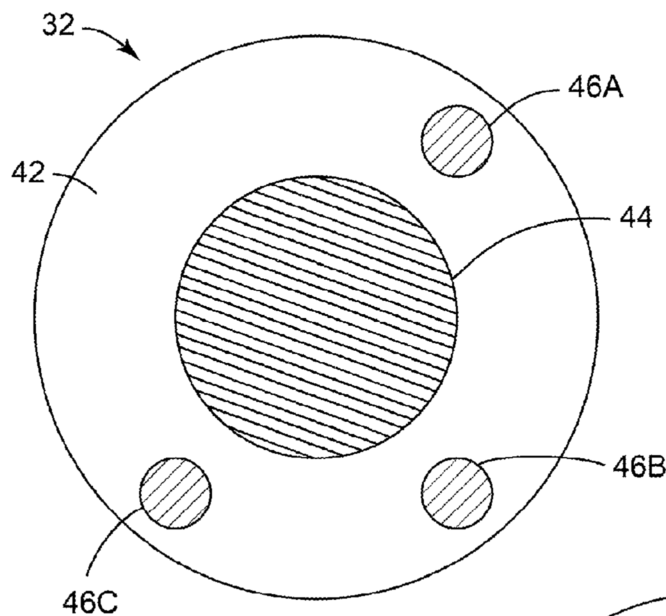
FIG. 5 is a conceptual diagram illustrating an example detection device with a surface that includes an acoustic sensor and multiple electrodes.

Each of detection devices 32*a*, 32*b* and 32*c* may be constructed in the shape of a cylinder, square, rectangle, or any other shape that facilitates hand-held manipulation and/or interaction with patient 11. In one example, the housings of detection devices 32*a*, 32*b* and 32*c* may be constructed in a circular puck-like shape that is easy for a user to hold against patient 11. Detection devices 32*a*, 32*b* and 32*c* may also be disposable or a single-use device or reusable between different patients. The housing of detection devices 32*a*, 32*b* and 32*c* may be sized such that the electrodes can generate an acceptable sensing vector to sense the electrical signals from the heart. An example arrangement of the acoustic sensor and the multiple electrodes are shown in FIG. 5.

Figure 4:
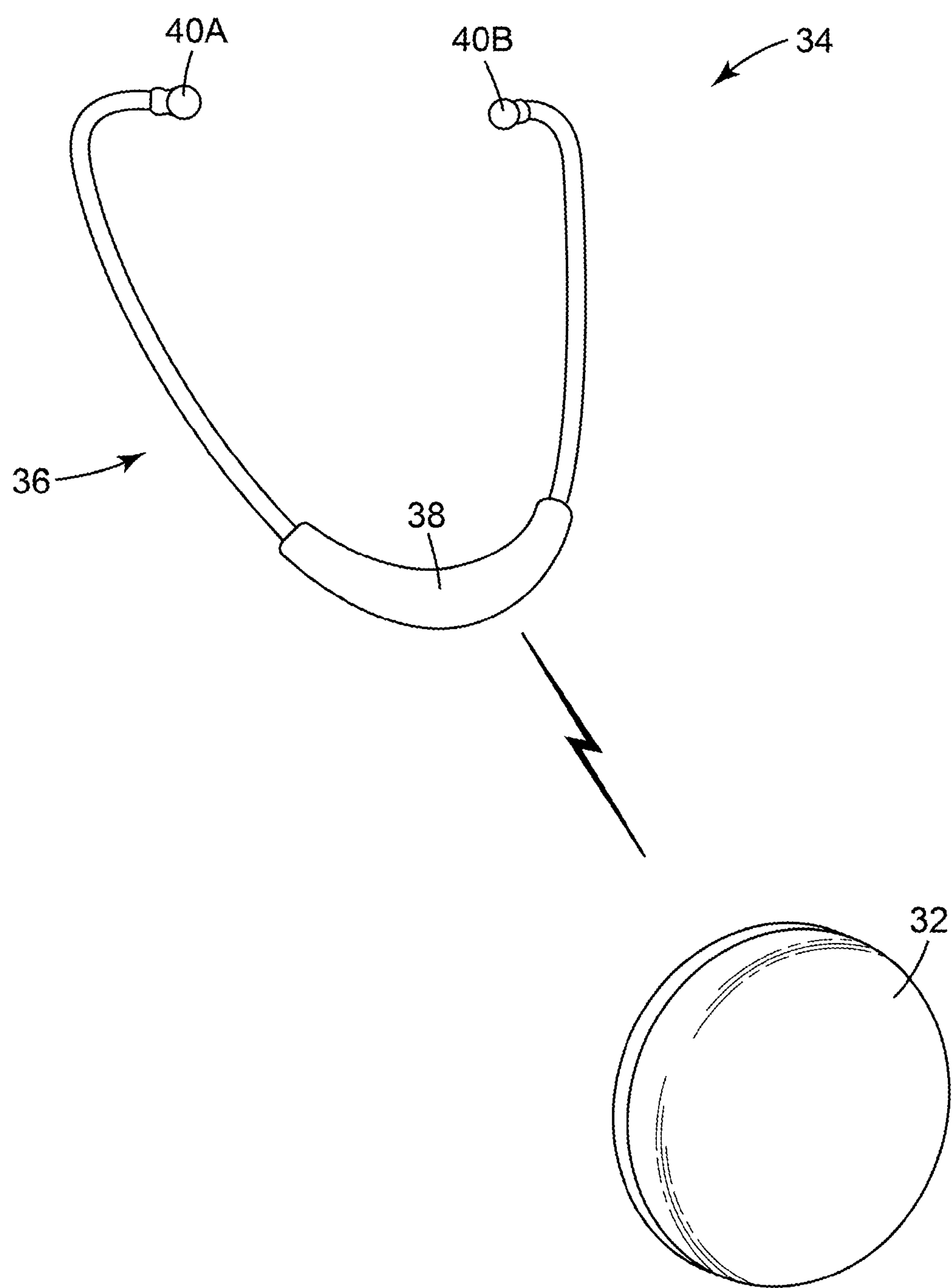
FIG. 4 is a conceptual diagram illustrating an example detection device configured to communicate with a wireless headset.

FIG. 4 is a conceptual diagram illustrating example system 34 that includes detection device 32 of FIG. 3 configured to communicate with wireless headset 36. As shown in FIG. 4, detection device 32 may wirelessly communicate with wireless headset 36. Detection device 32 may, for example, transmit acoustic signals, synchronized acoustic signals, and/or composite PCGs. In this manner, wireless headset 36 may present audio information to the user such as real-time acoustic signals detected by detection device 32, stored acoustic signals, and/or generated composite PCGs. For example, the user may listen or observe composite PCGs waveform loops from the patient that are triggered repeatedly by detection device 32 or in real-time by the ECG detected from the patient. Wireless headset 36 may be used alone or in conjunction with computing device 18, for example. In other examples, detection device 32 may communicate wirelessly to an electronic stethoscope instead of wireless headset 36. In some examples, the user may listen to the acoustic signals with an electronic or non-electronic stethoscope while viewing the composite PCG waveform and/or sound envelopes on a display (e.g., a display of computing device 18).

Wireless headset 36 may present or distribute audible information to the user via speakers 40A and 40B. Housing 38 may include processing circuitry, memory, one or more input/output devices, a telemetry module, and a rechargeable power source. Wireless headset 36 may communicate with multiple different detection devices 32, computing devices 18, or other devices. The telemetry module may utilize any short-range communication (e.g., Bluetooth or Near-Field Communication) or other wired or wireless communication protocols.

In one example, detection device 32 may include a visual indicator (e.g., a light such as an LED or a display) that indicates when one or more physiologically significant features of the acoustic signal are present in the signal. For example, detection device 32 may analyze the acoustic signal for S1 and/or S2 heart sounds. The visual indicator may blink each time the S1 heart sound is present. Alternatively, the visual indicator may light up with different colors to differentiate between S1 and S2 sound present in the acoustic signal. In this manner, the user of wireless headset 36 may listen to the real-time acoustic signal transmitted from detection device 32 and be prompted in real-time when one or more heart sounds are present in the signal. This indication may be helpful to train the user or focus the user when listening to the acoustic signal in a loud room. Instead of different color lights, detection device 32 may display different patterns, numbers, letters, symbols, or any other representation of the different heart sounds. In other examples, the visual indicator may indicate when a QRS complex or R-wave is detected in the ECG signal to identify when heart sounds may be upcoming. This visual indicator may also be provided on any other detection device herein, such as detection devices 12, 22, or 50.

In one example, detection device 32 (or detection device 12 or 22 and/or wireless headset 36, for example) may provide a learn mode in which one or more devices of system 34 generate an enhanced audio signal representative of the heart sounds of the patient. The enhanced audio signal may reduce noise or increase the amplitude of continually occurring heart sounds. A processor or module may analyze real-time acoustic signals detected from the patient. The processor may generate a composite PCG and use the composite PCG to filter acoustic signals, in real-time, before presenting the acoustic signals as sounds from the patient. This filter may be an adaptive filter that is either adapted to the patient during the learn mode or continually adapted as long as the acoustic signal is presented to the user. The adaptive filter may be applied to the live or real-time acoustic signals detected from the patient. In other examples, the processor may use other noise identification or noise cancelling techniques instead of a composite PCG to adjustably filter noise from the detected acoustic signals. Alternatively, the system may remove normal heart sounds (e.g., S1 and S2 heart sounds), noise, and/or increase the gain such that the user may listen to subliminal sounds or other sounds not normally detectable by the human ear amongst the normal sounds and noise.

An adaptive filter may utilize aspects of the composite PCG, such as the composite PCG representation of a temporal magnitude and frequency profile that may be unique to the patient. In one example, the temporal features identified in the composite PCG can be used to provide an optimized real-time adaptive set of frequency filters for each phase of the acoustic signal (e.g., a pre-S1 filter region, an S1 filter region, an S1-S2 gap region, an S2 region, a post-S2 region, an S3 region, and/or an S4 region). In another example, identified abnormal features on the composite PCG can be used to set and enhance a filter set during the time window of the acoustic signal (or live phonocardiogram) that corresponds to the time of the abnormal features. In another example, the composite PCG and respiration cycle information can be used to provide an optimized adaptive real-time filter that generates a consistent filtered acoustic signal to the user. In other words, the adaptive real-time filter may be constantly adjusted according to the breathing phase.

FIG. 5 is a conceptual diagram illustrating example detection device 32 of FIG. 3 with a surface that includes acoustic sensor 44 and multiple electrodes 46A, 46B, and 46C (collectively "electrodes 46"). As shown in FIG. 5, detection device 32 may include contact surface 42. Contact surface 42 may be the surface intended to contact the skin of patient 11. Contact surface 42 may be a portion of the housing of detection device 32. Acoustic sensor 44 may be disposed generally in the center of contact surface 42. In other examples, acoustic sensor 44 may be located away from the center of contact surface 42.

Detection device 32 may also include electrodes 46 disposed around the periphery of contact surface 42. Electrodes 46 may be arranged to increase the distance between each electrode to improve the sensing vector between each electrode. Although three electrodes 46 are shown in the example of FIG. 5, two electrodes or four or more electrodes may be provided in other examples. In alternative examples, acoustic sensor 44 and electrodes 46 may be disposed in other locations of surface 42.

Figure 6A:
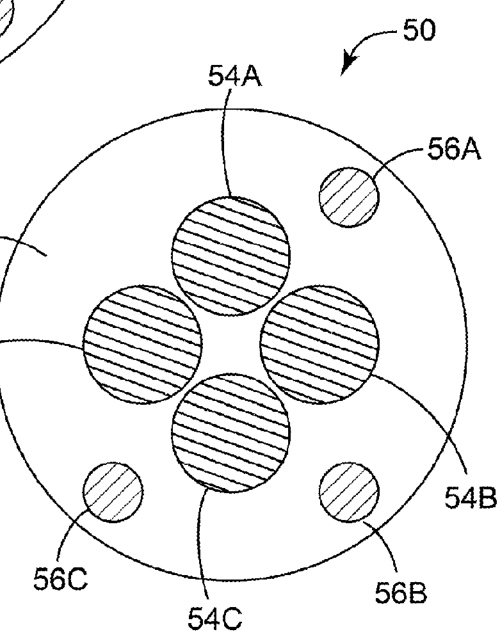
FIGS. 6A and 6B are conceptual diagrams illustrating an example detection device that includes a first surface with multiple acoustic sensors and a second surface with a user interface that displays information for positioning the detection device on a patient.
Figure 6B:
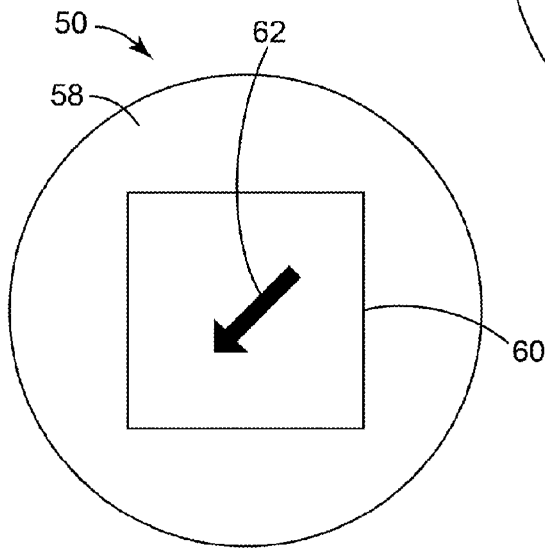

FIGS. 6A and 6B are conceptual diagrams illustrating example detection device 50. Detection device 50 may be similar to detection device 32 of FIG. 3. As shown in FIG. 6A, detection device 50 may include contact surface 52 configured to contact the skin of patient 11. Detection device 50 may also include multiple electrodes 56A, 56B, and 56C for detecting electrical signals from the heart. Multiple electrodes 56 may be provided to allow detection device 50 to select the optimal sensing vector for an electrogram that may synchronize the acoustic signals.

Detection device 50 may also include multiple acoustic sensors 54A, 54B, 54C, and 54D (collectively "acoustic sensors 54") disposed on contact surface 52. Acoustic sensors 54 may provide acoustic sensors 54 to facilitate positioning of detection device 50 over a desired intercostal space of patient 11. Detection device 50 may monitor the acoustic signals detected from each of acoustic sensors 54 and provide feedback to the user in the form of a direction in which the user should move detection device 50. In this manner, detection device 50 may aid the user in determining the position at which the strongest acoustic signals can be detected from patient 11. Although four acoustic sensors 54 are provided in detection device 50, fewer or greater acoustic sensors may be utilized in other examples.

For example, detection device 50 may compare the acoustic signals detected from each of acoustic sensors 54. The acoustic signal having the strongest amplitude, for example, may indicate that detection device 50 should be moved in the direction of the acoustic sensor 54 that sensed the strongest signal. FIG. 6B illustrates an example user interface 60 that displays the direction in which the user should move detection device 50. Surface 58 may include user interface 60 (e.g., a display) that provides an arrow (e.g., arrow 62), reference characters (e.g., pluses and minuses) that relate to the position of each acoustic sensor 54 (e.g., a plus may indicate the acoustic signal is stronger in that direction), different colored lights, or any other indication of the direction in which detection device 50 should be moved.

In other examples, detection device 50 may provide feedback for positioning the device on patient 11 with only a single acoustic sensor. Detection device 50 may include an accelerometer (e.g., a two or three axis accelerometer or multiple single axis accelerometers) and the single acoustic sensor. Detection device 50 may monitor the output of the accelerometer and the acoustic signal. If the acoustic signal increases in strength or intensity as detection device 50 is moved, detection device 50 may provide feedback to continue moving detection device 50 in that same direction. Conversely, if the acoustic signal decreases in strength or intensity as detection 50 is moved, detection device 50 may provide feedback to reverse or otherwise change the direction of movement with respect to patient 11. If the acoustic signal does not change or decreases again, detection device 50 may continue to provide feedback that indicates which way the user should move detection device 50. In this manner, detection device 50 may facilitate finding an effective position (e.g., an ideal intercostal space) to detect acoustic signals from the heart with minimal trial and error by the user. For example, the visual or audio signal may be used to optimize the S1 sound from the apex and L4 positions or to optimize the S2 sound from the 2R and 2L positions on patient 11.

Figure 7:
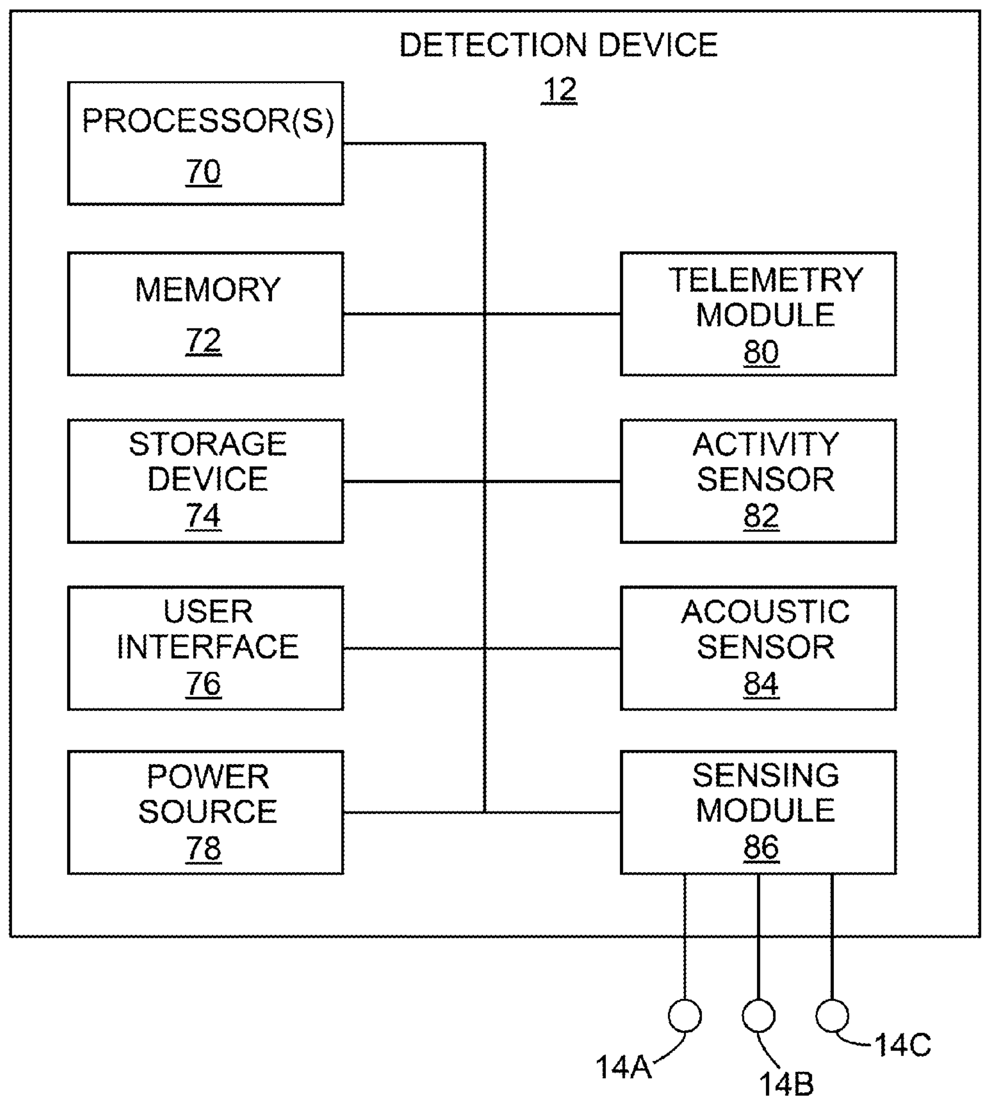
FIG. 7 is a block diagram illustrating components of one example of the detection device shown in FIG. 1.

FIG. 7 is a block diagram illustrating components of one example of detection device 12 shown in FIG. 1. FIG. 7 illustrates only one particular example of detection device 12, and many other example embodiments of detection device 12 may be used in other instances. For example, detection device 12 may include additional components or fewer components. Moreover, the example components shown in FIG. 7 may be used for any of detection devices 22, 32, 50 of FIGS. 3-6. As shown in the specific example of FIG. 7, detection device 12 includes one or more processors 70, memory 72, storage device(s) 74, user interface 76, power source 78, telemetry module 80, activity sensor 82, acoustic sensor 84, and sensing module 86. Detection device 12 may also includes an operating system, which may include modules and/or applications that are executable by processors 70 and detection device 12. Each of components 70, 72, 74, 76, 78, 80, 82, and 84 may be interconnected (physically, communicatively, and/or operatively) for inter-component communications.

Processors 70, in one example, are configured to implement functionality and/or process instructions for execution within detection device 12. For example, processors 70 may be capable of processing instructions stored in memory 72 or instructions stored on storage devices 74. These instructions may define or otherwise control the operation of detection device 12.

Memory 72, in one example, is configured to store information within detection device 12 during operation. Memory 72, in some examples, is described as a computer-readable storage medium. In some examples, memory 72 is a temporary memory, meaning that a primary purpose of memory 72 is not long-term storage. Memory 72, in some examples, is described as a volatile memory, meaning that memory 72 does not maintain stored contents when the computer is turned off. Examples of volatile memories include random access memories (RAM), dynamic random access memories (DRAM), static random access memories (SRAM), and other forms of volatile memories known in the art. In some examples, memory 72 is used to store program instructions for execution by processors 70. Memory 72, in one example, is used by software or applications running on detection device 12 to temporarily store information during program execution.

Storage devices 74, in some examples, also include one or more computer-readable storage media. Storage devices 74 may be configured to store larger amounts of information than memory 72. Storage devices 74 may further be configured for long-term storage of information. In some examples, storage devices 74 include non-volatile storage elements. Examples of such non-volatile storage elements include magnetic hard discs, optical discs, floppy discs, flash memories, or forms of electrically programmable memories (EPROM) or electrically erasable and programmable (EEPROM) memories.

Detection device 12, in some examples, also includes a telemetry module 80. Detection device 12, in one example, utilizes telemetry module 80 to communicate with external devices such as computing device 18 or wireless headset 34. Telemetry module 80 may include an optical transceiver, a radio frequency transceiver, or any other type of device that can send and receive information. Other examples of such telemetry modules may include Bluetooth, 3G, 4G, and WiFi radios in mobile computing devices as well as USB. In some examples, computing device 12 utilizes telemetry module 80 to communicate with external devices (e.g., computing device 18) a server, mobile phone, or other computing device.

Detection device 12, in one example, also includes one or more user interfaces 76. User interface 76 may be configured to receive input from a user (e.g., tactile, audio, or video feedback). User interface 76 may include a touch-sensitive and/or a presence-sensitive screen, a voice responsive system, or any other type of device for detecting a command from a user. User interface 76 may include a display for presenting visual information (e.g., a composite PCG) or audio information (e.g., playback of acoustic information or a composite PCG). For example, user interface 76 may include a sound generation device configured to present the composite PCG audibly to a user. The sound generation device may be an electro-acoustic transducer for converting electric signals into sounds (e.g., a speaker or headphone).

In some examples, playback of the acoustic information and/or composite PCG may be augmented to aid the user in identification of heart sounds. For example, user interface 76 may present a slowed down real-time playback of acoustic information. The slowed playback may incorporate any filtering or analysis described herein. This slowed down audio playback may be useful for young patients or other patients with higher heart rates. This slowed down playback may be synchronized with the actual (i.e., real-time) heart rate such that one slowed down heart beat occurs within 2, 3, 4, etc. real-time heart beats. Non-synchronized playback may also be provided to the user. The playback speed may be selected by the user via one or more inputs provided by user interface 76.

Detection device 12 may also include one or more activity sensors (e.g., one or more accelerometers, mercury switches, micromechanical systems (MEMS) accelerometers, and/or one or more gyroscopes) that may detect movement of detection device 12. Detection device 12 may include one or more acoustic sensor 84 that senses and detects an acoustic signal from the heart. In addition, detection device 12 may include a sensing module that detects electrical signals from one or more of electrodes 14 electrically coupled to sensing module 86. Detection device 12 may also include one or more power sources 78, such as a rechargeable or non-rechargeable battery that may provide power to detection device 12. Power sources 78, in some examples, may be made from nickel-cadmium, lithium-ion, or other suitable materials. In other examples, power sources 78 may be capable of providing stored power or voltage from another stored energy (e.g., fuel cells or capacitors).

Figure 8:
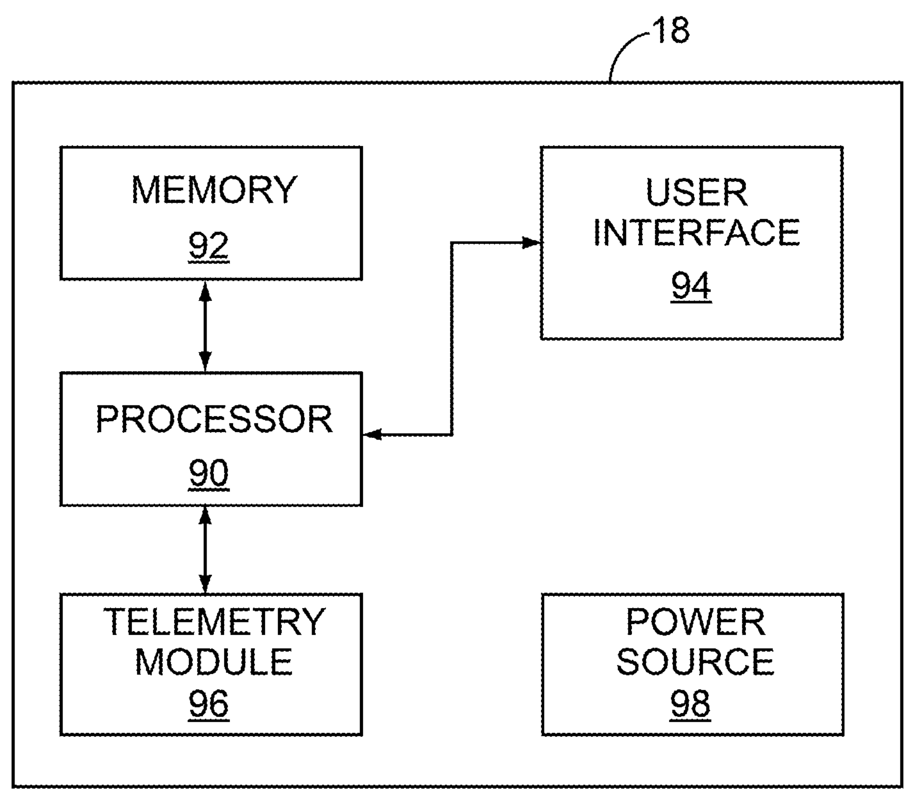
FIG. 8 is a block diagram illustrating components of one example of the computing device shown in FIG. 1.

FIG. 8 is a block diagram illustrating components of computing device 18 shown in FIGS. 1-3. As shown in FIG. 8, computing device 18 may include a processor 90, memory 92, user interface 94, telemetry module 96, and power source 98. Memory 92 may store instructions that, when executed by processor 90, causes processor 90 and computing device 18 to provide the functionality ascribed to computing device 18 throughout this disclosure. For example, processor 90 may be configured to generate composite PCGs from synchronized acoustic information using ECG information.

In general, processor 90 comprises any suitable arrangement of hardware, alone or in combination with software and/or firmware, to perform the techniques attributed to computing device 18, and processor 90, user interface 94, and telemetry module 96. In various examples, computing device 18 may include one or more processors, such as one or more microprocessors, DSPs, ASICs, FPGAs, or any other equivalent integrated or discrete logic circuitry, as well as any combinations of such components. Computing device 18 also, in various examples, may include a memory 92, such as RAM, ROM, PROM, EPROM, EEPROM, flash memory, a hard disk, a CD-ROM, comprising executable instructions for causing the one or more processors to perform the actions attributed to them. Moreover, although processor 90 and telemetry module 96 are described as separate modules, in some examples, processor 90 and telemetry module 96 are functionally integrated. In some examples, processor 90 and telemetry module 96 correspond to individual hardware units, such as ASICs, DSPs, FPGAs, or other hardware units.

Memory 92 may store instructions that, when executed by processor 90, cause computing device 18 to provide the functionality ascribed to computing device 18 herein. User interface 94 may include a button or keypad, lights, a speaker for voice commands, a display, such as a liquid crystal (LCD) or light-emitting diode (LED). In some examples the display may be a touch screen. User interface 94 may also include a sound generation device, audio output, or some other component for outputting audio information (e.g., real-time acoustic signals or a composite PCG) to the user. For example, the sound generation device may be an electro-acoustic transducer for converting electric signals into sounds (e.g., a speaker or headphone). Telemetry module 96 may support wireless communication between detection device 12 and computing device 18, for example.

Figure 9:
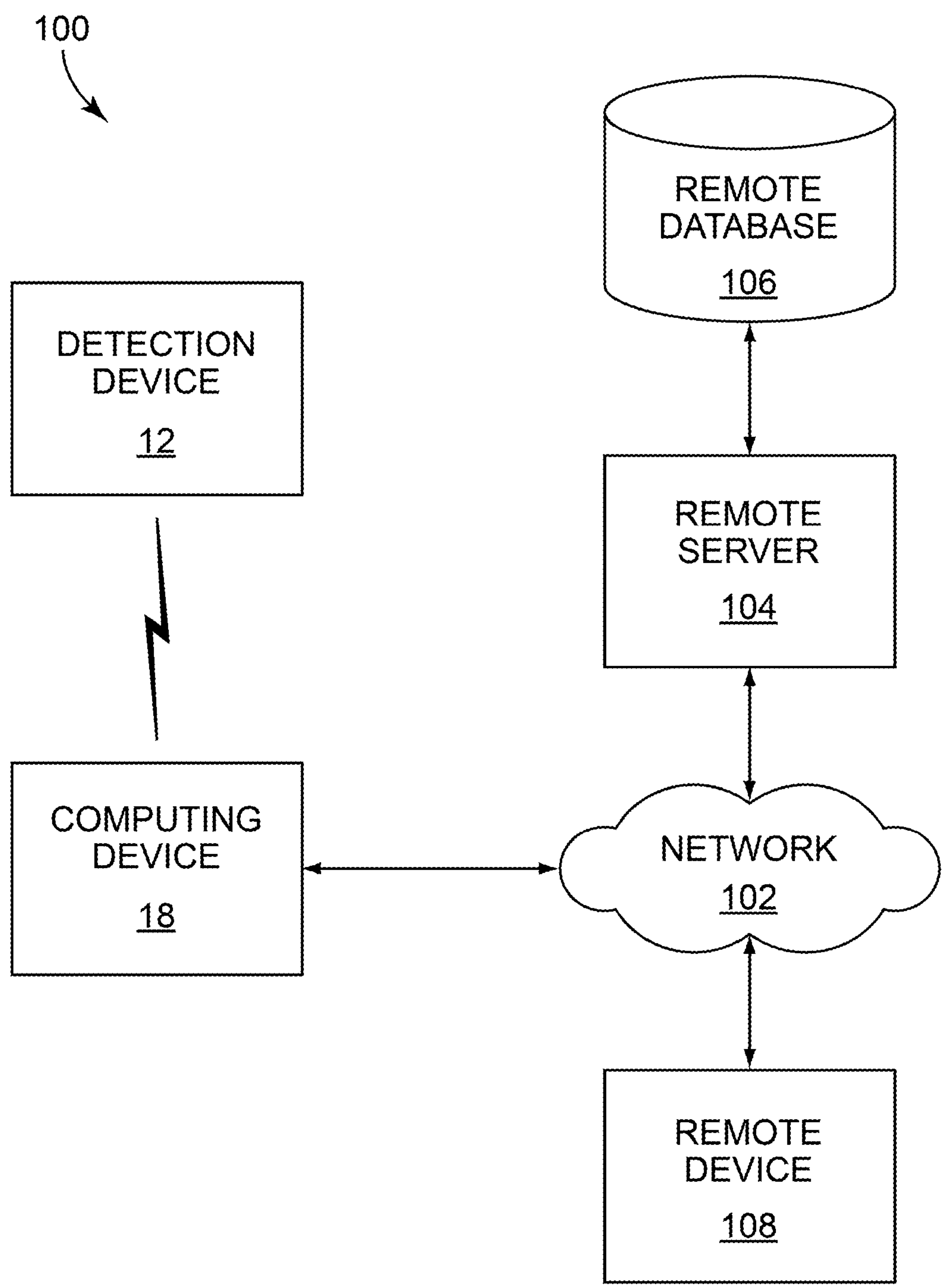
FIG. 9 is a conceptual diagram illustrating an example system for distributing acoustic and electrical information detected from a patient over a network.

FIG. 9 is a conceptual diagram illustrating system 100 for distributing acoustic and electrical information detected from a patient over network 102. As shown in FIG. 9, any information detected or generated by detection device 12 and/or computing device 18 may be transmitted to remote devices or systems. In this manner, detection device 12 and/or computing device 18 may distribute one or more processing tasks (e.g., generation of composite PCGs) to remote server 104 or remote device 108. System 100 may include detection device 12, computing device 18, network 102, remote server 104, remote database 106, and remote device 108.

Computing device 18 may transmit detected acoustic signals, detected electrical signals, composite PCGs, or any other information to remote server 104 or remote device 108. Remote server 104 provides an operating environment for a hosted diagnostic service or other support service for detection device 12. For example, remote server 104 may execute software to compare a composite PCG from a patient to one or more heart sound pathologies stored in remote database 106. The stored pathologies may be pathologies stored from other patients and/or models of pathologies based on sounds from one or more patients. Remote server 104 may then identify one or more matching pathologies and transmit a diagnosis back to computing device 18 for review by the clinician. In other examples, remote database 106 may store historical or previous composite PCGs generated for patient 11. Remote server 104 may then identify any changes and relay such past patient data back to computing device 18 and/or remote device 108, with such communications occurring in real-time in the presence of the patient via a detection device or offline by remote access.

Remote device 108 may be a computing device operated by a remote clinician. The remote clinician may be a primary care physician of the patient or an expert at reviewing PCG data. In this manner, the patient may separately use detection device 12 and send the resulting information to a remote clinician via network 102. System 100 may support such distributed computing and sharing of information to enable the functions described herein and diagnosis of the patient. System 100 may also be used by a clinician to review past acoustic signals and/or composite PCGs to learn heart sound pathologies and improve diagnostic technique.

In other examples, detection device 12 may include a cellular radio module or other network interface that allows detection device 12 to directly transmit and/or receive data over network 102. Detection device 12 may connect to an access point with access to network 102 without interfacing with computing device 18. Alternatively, detection device 12 may include components of computing device 18 that may allow detection device 12 to communicate with remote device 108 or remote server 104 via network 102.

Figure 10:
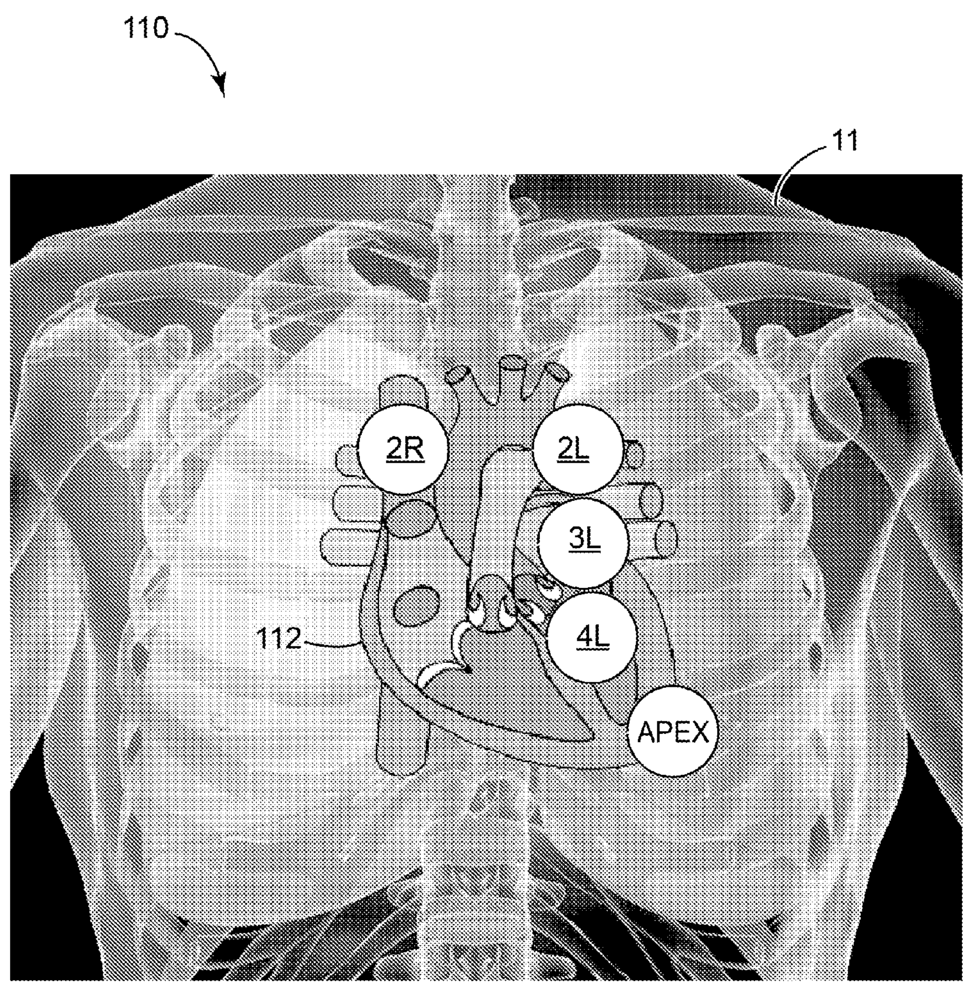
FIG. 10 is a conceptual diagram illustrating possible anatomical locations at which a detection device may be positioned against a patient.

FIG. 10 is a conceptual diagram illustrating possible anatomical locations at which a detection device (e.g., detection device 12) may be positioned against patient 11. As shown in FIG. 10, acoustic signals may generally be obtained from different locations on patient 11. Each location 2R, 2L, 3L, 4L, and APEX may correspond to a different intercostal space between adjacent ribs. Each location may provide higher magnitude acoustic signals from proximate structures of heart 112. In some examples, detection device 12 may be positioned at the 2L or 4L location to detect an acoustic signal. In other examples, detection device 12 may be positioned at the 3L location in an attempt to obtain acoustic signals from most, if not all, structures associated with heart 112.

Figure 11:
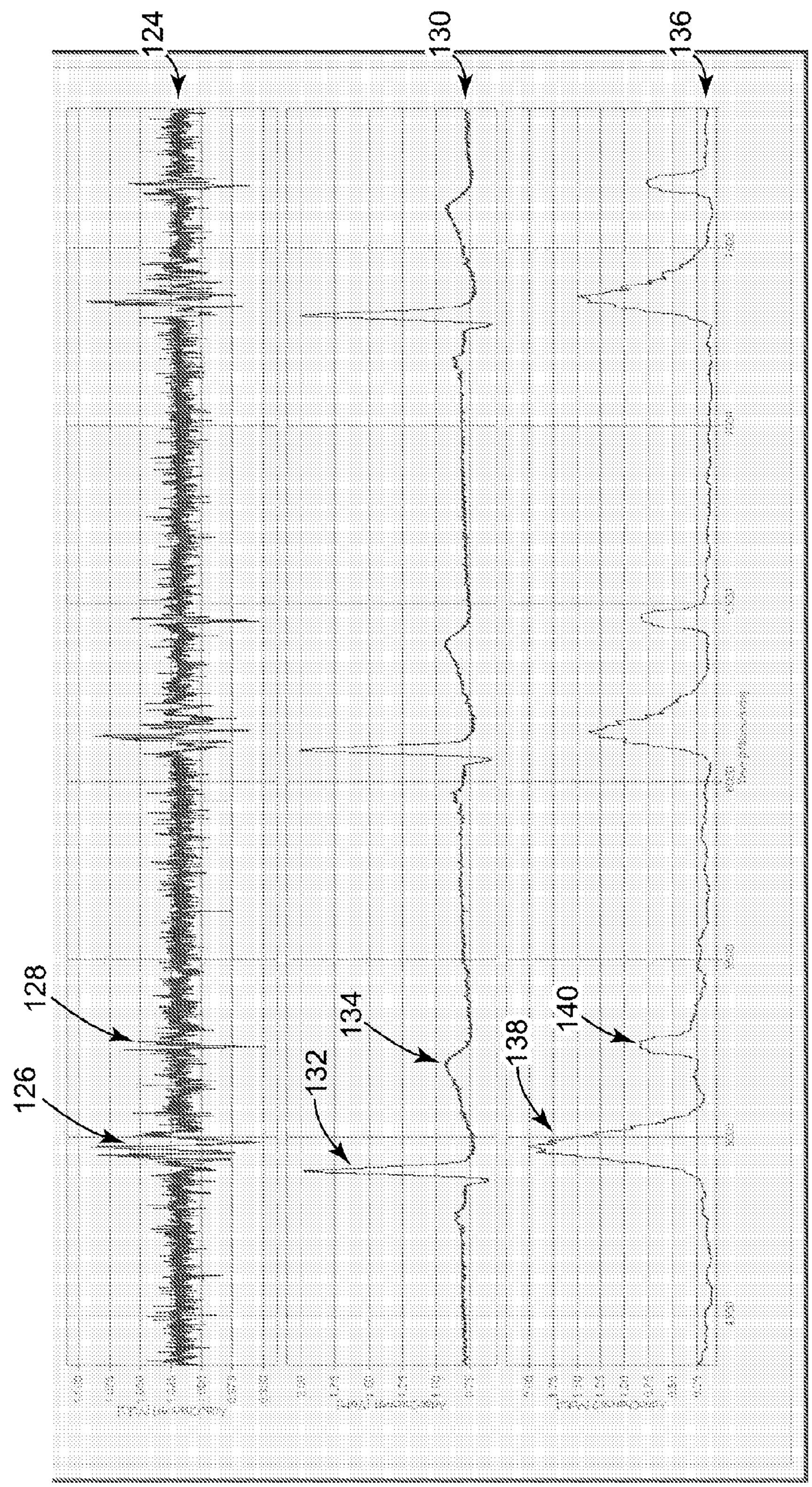
FIG. 11 is a graph of example electrical signals and acoustic signals detected from a patient.

FIG. 11 is a graph of example electrical signals and acoustic signals detected from patient 11. As shown in FIG. 11, acoustic signal 124 may be a raw acoustic signal as detected by an acoustic sensor. In other words, acoustic signal 124 may include noise from breathing sounds, gastrointestinal sounds, movement of the acoustic sensor on the skin, and any other unintended sounds. Acoustic signal 124 may still include identifiable features such as the S1 heart sound and features as the S2 heart sound.

Electrical signal 130 may provide a representation of the electrical activity of the heart. Electrical signal 130 may include R-wave 132 and T-wave 134. R-wave 132 may indicate depolarization of the left and right ventricles and be used as a trigger to synchronize acoustic signals from the same cardiac cycle. In other words, each R-wave may be used to establish timing of the acoustic signals and where each heart sound (e.g., normal S1 and S2 heart sounds) should occur within each cardiac cycle.

While early features in the ECG waveform are used to synchronize the sound averaging, other features in the PCG waveform (e.g. S2) can be added to provide additional temporal fidelity by incorporating later ECG trigger features (e.g. T-wave). By using multiple triggering features in the ECG waveform, synchronization of the heart sound features can be improved.

T-wave 134 represents the repolarization of the heart and may be more closely associated with the later heart sounds as the pulmonary and aortic valves close. One could use R-wave 132 as the primary triggering feature and provide further augmentation by adding additional triggering features, such as T-wave 134. In addition, the two different triggering features can be used in a synergistic or complimentary fashion as triggering features.

In one embodiment, alternate triggering features in the ECG waveform can be used in patients with abnormal ECG patterns (e.g. diminished or inverted R-wave). For example, the system may be programmed to recognize an abnormal cardiac cycle which may have a weak R-wave that does not meet the triggering threshold. In such a situation, the system may automatically switch to an alternative triggering feature, such as a T-wave. This is particularly useful because for different cardiac diseases, the primary trigger feature may not be evident. Thus, the ability to automatically switch to a different triggering feature can be critical in diagnosing an abnormality.

Acoustic signal 136 may be generated from acoustic signal 124. As depicted, the acoustic signal 136 represents the power of acoustic signal 124. In other words, acoustic signal 136 may represent the magnitude of the heart sounds detected from the patient. Envelope 138 may be a peak representing the S1 heart sound and envelope 140 may be the peak representing the S2 heart sound.

Figure 12A:
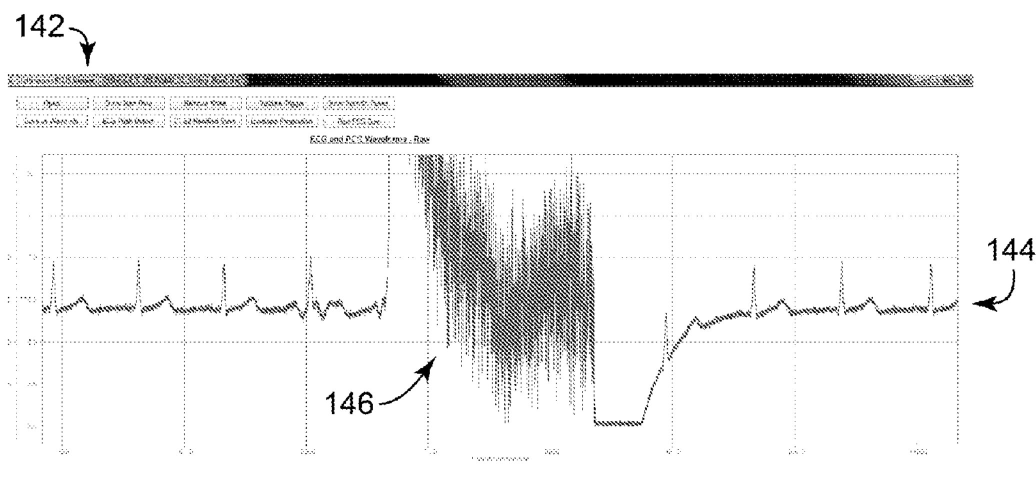
FIGS. 12A and 12B are graphs illustrating an example noise artifact in an electrocardiogram and removal of the noise artifact.
Figure 12B:
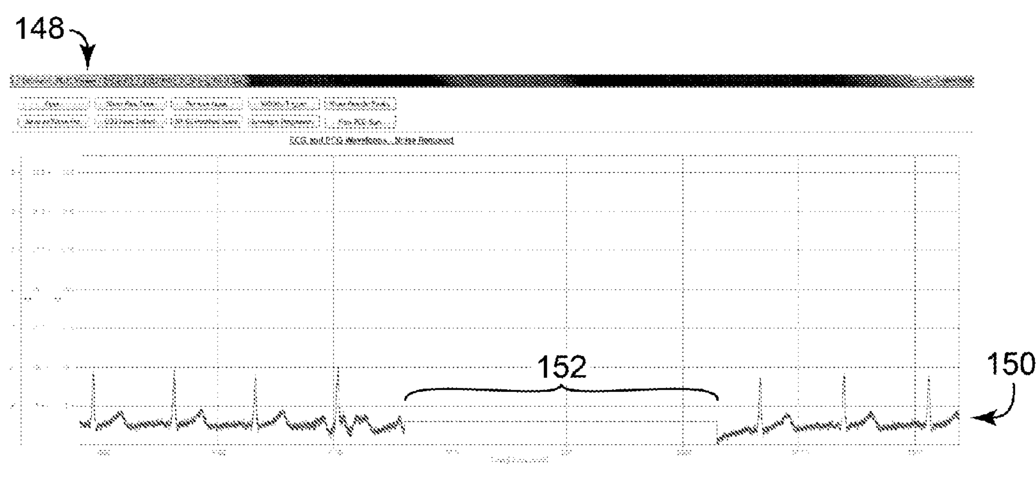

FIGS. 12A and 12B are graphs 142 and 148 illustrating an example noise artifact 146 in electrocardiogram (ECG) 144 and removal of noise artifact 146 in ECG 150. As shown in FIG. 12A, ECG 144 may be an electrical signal that includes noise artifact 146. System 10 may remove noise artifact 146 as an initial step to processing the ECG or detected electrical signal 144 for trigger events (e.g., R-waves).

System 10 may preprocess the electrical signal using ratio metric noise removal. This process may include assessing signal maximums and minimums based on a typical 1 Hz ECG period and assess the signal in discrete blocks. Then, system 10 may traverse the signal using 2 second length sample blocks, for example, to ensure assessment of maximum and minimum values over one or more ECG periods. System 10 may collect maximum and minimum values for each block and create a list of the maximum and minimum values. System 10 may average the maximum values, average the minimum values, and the traverse ECG signal 144. When traversing ECG signal 144, system 10 may reject values 10% or more above the average maximum or 10% or more below the average minimum. Further, system 10 may replace a portion (e.g., ⅛th of a second) surrounding the rejected values with an average value of the signal. System 10 may then process the remaining ECG signal with a low-pass filter. Other noise rejection methods may include statistical methods for rejection of outliers (e.g., portions of data that exceed a specified number of standard deviations from the normal population may be rejected).

Graph 148 may represent the resulting ECG signal 150 that has had noise artifact 146 removed from the signal. Section 152 indicates the area of the signal that has been cleared of noise artifact 146. This process may remove any noise artifacts that may interfere with detecting the R-waves and peaks of R-waves needed to identify a trigger for synchronizing the acoustic signals. In other words, identified noise sections of ECG signal 150 (e.g., a data stream) may be removed from further processing such that these sections are not used in the generation of a composite PCG.

In other examples, activity sensor 82 may be used to filter noise from patient movement. For example, system 10 may monitor the output of activity sensor 82 or another accelerometer to blank out or remove acoustic information from the acoustic signals when movement of the patient is detected. Alternatively, system 10 may amplify or target portions of the acoustic signals when a desired activity or physical maneuver is identified from the output of activity sensor 82. In some examples, the acoustic data may undergo noise rejection processing similar to that of ECG signal 150. The identified noise sections of the acoustic data may similarly be removed from further processing.

Figure 13:
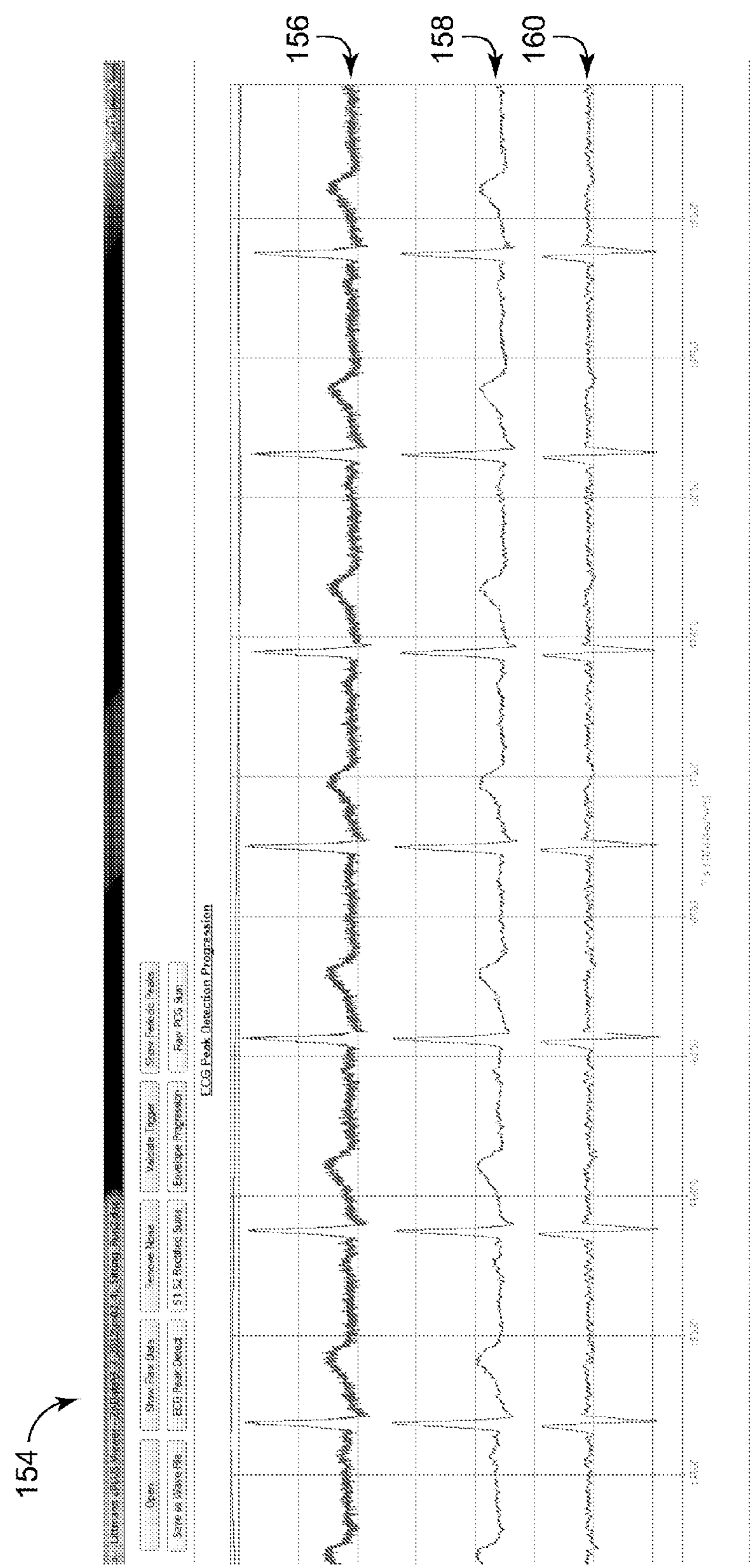
FIG. 13 is a graph illustrating an example electrocardiogram, a filtered electrocardiogram, and a differential signal from the filtered electrocardiogram.

FIG. 13 is a graph illustrating an example ECG 156, filtered ECG 158, and differential signal 160 from filtered ECG 158. As shown in FIG. 13, system 10 may begin to process the detected ECG to identify an R-wave peak by calculating trigger levels for identifying a rising edge of the R-wave of each cardiac cycle. The detected, or raw, ECG 156 may first be filtered as described with respect to FIGS. 12A and 12B. System 10 may then generate filtered ECG 158 by filtering noise and/or statistical outliers from ECG 156.

Next, system 10 may differentiate filtered ECG 158 to generate differential signal 160. System 10 may assess differential signal 160 for a maximum positive slope. System 10 may then generate the R-wave trigger value at approximately 50% of the maximum positive slope. System 10 may then use the R-wave trigger value to detect each R-wave from differential signal 160. In other examples, system 10 may use alternative methods to detect R-wave peaks (e.g., peak detection). These alternative methods include, without limitation, polynomial or wavelet detection.

System 10 may traverse differential signal 160 while applying the R-wave trigger value to determine each R-wave peak. This traversal of differential signal 160 may include a linear search of differential signal 160 and identification of the initial value greater than the R-wave trigger value. For each initial trigger point that exceeds the R-wave trigger value, system 10 may time stamp the initial trigger point. At the subsequent zero crossing of differential signal 160, system 10 may identify the crossing as an R-wave peak candidate and time stamp the R-wave peak candidate.

System 10 may then review the last detected peak time stamp and reject the current peak if the time delta is less than an expected delta between R-wave peaks (e.g., approximately 250 milliseconds (ms), for example). System 10 may also review the initial trigger time stamp and reject the current peak candidate if the delta time is between the initial trigger time stamp and the peak time stamp is less than approximately 50 ms. If the current R-wave peak candidate is not rejected, then system 10 may add the zero crossing time stamp and original ECG magnitude value to a R-wave peak list for further assessment if desired.

Figure 14:
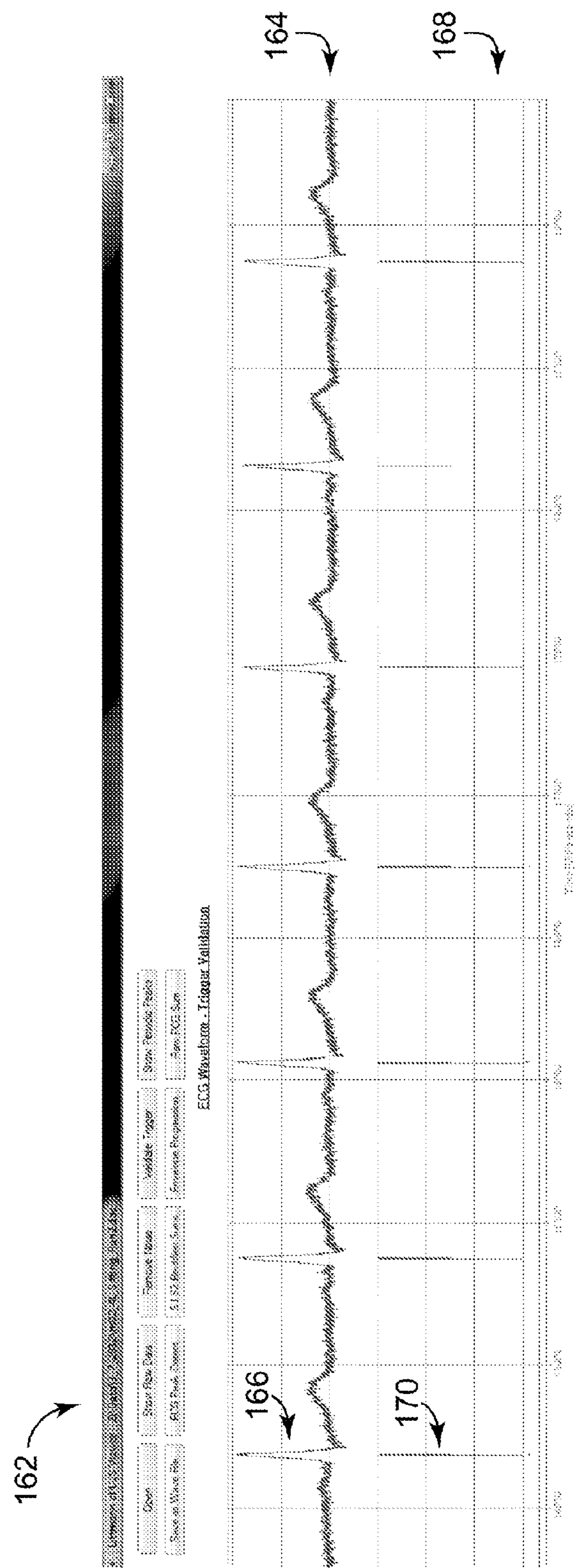
FIG. 14 is a graph illustrating an example electrocardiogram and detection of r-wave peaks from each cardiac cycle in the electrogram.

FIG. 14 is graph 162 illustrating an example ECG 164 and detection of R-wave peaks 168 from each cardiac cycle in ECG 164. R-wave 166 in ECG 164 may be identified using the algorithm described in FIG. 13. R-wave peak display 170 may be one of R-wave peaks 168 and generated from the filtered ECG 164. R-wave peak display 170 may represent the time at which system 10 has identified R-wave 166 within the cardiac cycle.

Figure 15:
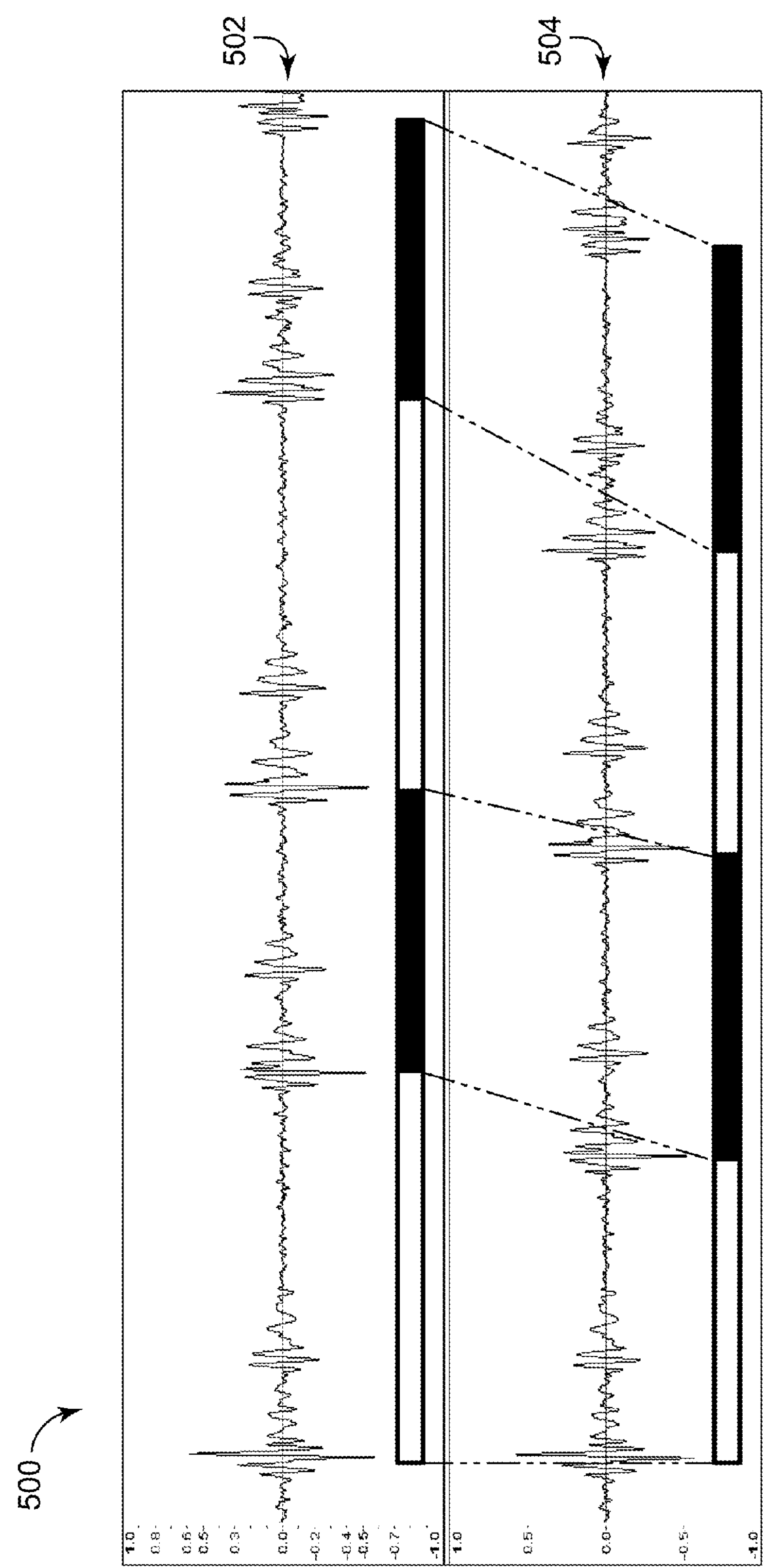
FIG. 15 is a graph illustrating an example electrocardiogram with an arrhythmia, and a revised electrocardiogram with the arrhythmia portions removed.

A number of patients have heart arrhythmias that result in the PCG heart sound being produced at irregular intervals. This can be distracting for the clinician when trying to focus on specific features within the PCG, impeding assessment and diagnosis of any heart conditions. The irregular heart rhythm can be transformed into a regular period by capturing a predetermined time window before and after the ECG triggering event and appending (or "stitching") the PCG from each time window. This is illustrated in graph 500 of FIG. 15. PCG 502 shows an example phonocardiogram with an arrhythmia. PCG 504 shows a revised phonocardiogram with a regular rhythm. As an additional feature, the heart rate of the synthesized PCG can be modified by changing the interval between each time window.

Alternatively, the PCG from the time window of one heart contraction, or multiple time windows from selected heart contractions, can be appended to itself to form a continuous periodic waveform.

Figure 16:
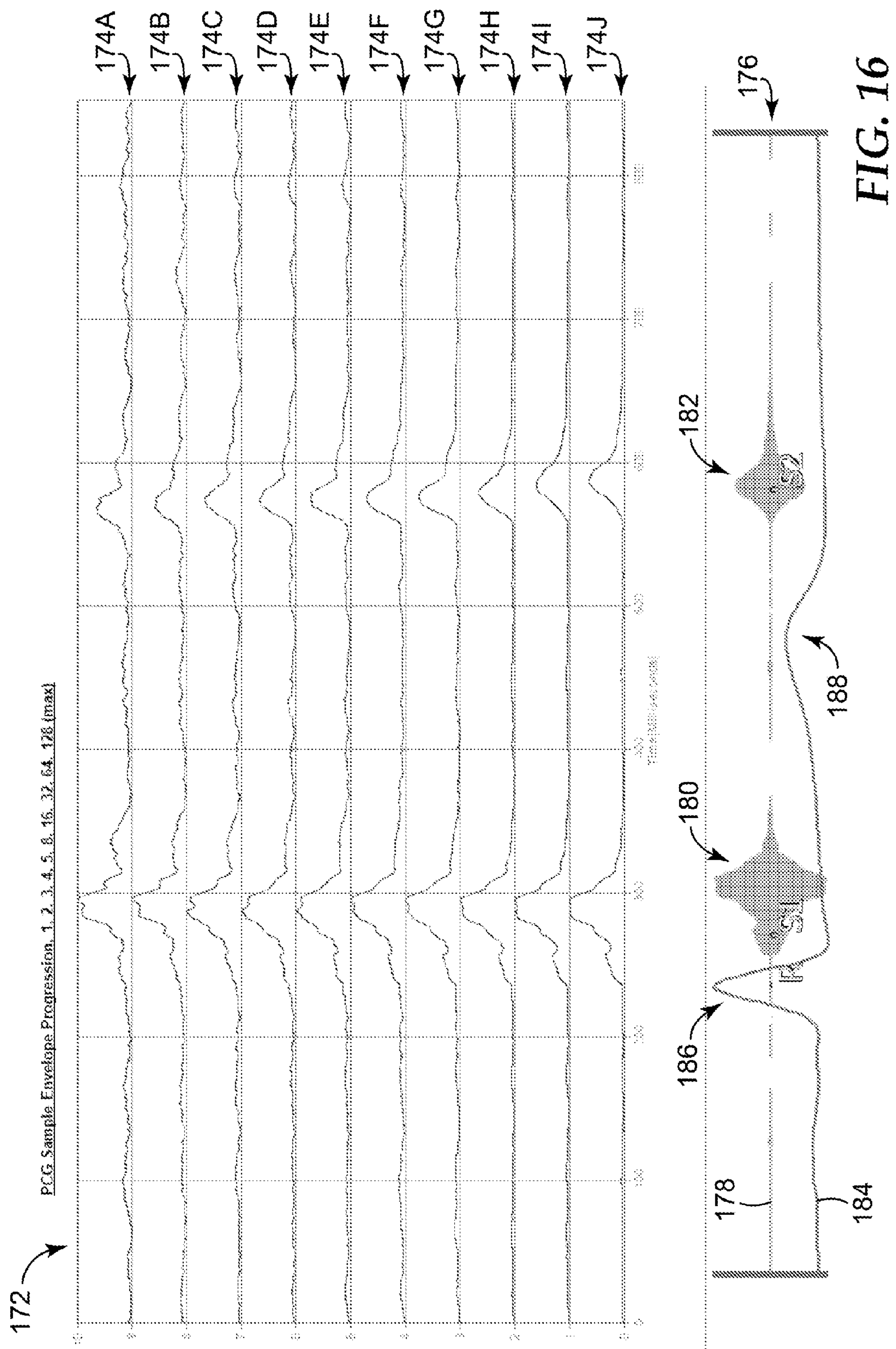
FIG. 16 is a graph illustrating an example progression for generating a composite PCG from synchronized acoustic signals.

FIG. 16 is a graph illustrating an example progression for generating composite PCG 176 from synchronized acoustic signals. As shown in FIG. 16, multiple acoustic signals may be averaged (or summed) to generate composite PCG that minimizes noise evident in individual acoustic signals. First, system 10 may filter the acoustic signal with a band pass filter (e.g., a 30-400 Hz filter). Then, system 10 may synchronize the acoustic signals for each cardiac signal. Using the R-wave peak list generated above, system 10 may traverse the R-wave peak list and calculate the average ECG period by averaging the time between each R-wave peaks. System 10 may then traverse the R-wave peak list and assemble the average of acoustic signal data over two ECG periods, one period before each peak and one period after each peak.

Once the acoustic signals are synchronized for each cardiac cycle, system 10 may average the acoustic signals. Averaged acoustic signals 174A through 174J illustrate the progression of the acoustic signals as more and more signals are averaged. Acoustic signal 174J results in a relatively smooth signal with most noise reduced or removed from the signal. The waveform of acoustic signal 174J may then be mirrored with respect to the axis to produce composite PCG 176. Any composite PCG may be generated by averaging acoustic signals from two or more cardiac signals. The composite PCG 176 may be generated to represent idealized images of phonocardiograms typically presented in medical textbooks and used to train clinicians.

The systolic S1 heart sounds and diastolic S2 heart sounds of composite PCG 176 may be detected after composite PCG 176 has been generated. System 10 may then preprocess the PCG using statistical noise removal. System 10 may assess signal maximums and minimums based on a typical 1 Hz ECG period and assess the signal in discrete blocks. System 10 may traverse the signal using 2 second length sample blocks to fully assess maximum and minimum values over one or more ECG periods. System 10 may then collect maximum and minimum values for each block and create a list of these maximum and minimum values. The sum of the maximum values and the sum of the minimum values may then be calculated.

System 10 may create a reject level for the maximum values by adding 1 standard deviation to the average maximum. In addition, system 10 may create a reject level for the minimum values by subtracting 1 standard deviation from the average minimum. System 10 may then insert the overall average value into a block of 256 samples surrounding any rejected data to flatten any noise still present in the graph.

System 10 may also provide additional filtering to the acoustic signals detected from the patient. For example, one or more band pass filters may be applied to the acoustic signal to reduce low and high frequency noise. System 10 may filter any noise in the composite PCG data using a 30 Hz to 400 Hz Butterworth filter and a 4 pole band pass filter. Alternatively, system 10 may perform a short time Fourier transform on the acoustic signal to remove noise. If smaller frequency ranges are desired, the acoustic signal may be additionally filtered to one or more smaller frequency bands to identify sounds within these frequencies. The filtered acoustic signals may then be subjected to root mean square (RMS) power (or average) calculations before the acoustic signals are incorporated into the composite PCG. System 10 may then aggregate a representative period using time synchronized averaging. System 10 may perform a RMS calculation on the resultant period signal and differentiate the resultant signal to facilitate peak detection that is used to extract different envelopes (e.g., the S1 and S2 heart sounds). Each of the processed acoustic signals (synchronized power spectra for each cardiac cycle) may be stored for each frequency band generated above. In some examples, the synchronized acoustic signals may be subjected to a short time Fourier transform and then integrated to create a composite PCG waveform for each frequency band.

Using the composite PCG, system 10 may calculate the S1 and S2 trigger and release points by identifying when the composite PCG and a derivative of the composite PCG exceed a specific threshold. For example, system 10 may create a derivative by differentiating the composite PCG. In certain potentially advantageous implementations, the specific threshold trigger and release points are identified in a prescribed time window that is referenced to an R-wave trigger. In some examples, trigger points for the S1 heart sound may be created using 30% of the composite PCG range and 15% of the differentiated composite PCG range. Trigger points for the S2 heart sound may be created using 15% of the composite PCG range and 8% of the differentiated composite PCG range. System 10 may then search the composite PCG and the differentiated composite PCG waveforms linearly, from the R-wave peak, and look for first value greater than the S1 trigger point. Subsequently, system 10 may traverse the differentiated composite PCG and identify the point at the zero crossing as representing the S1 peak. System 10 may validate the S1 peak. For example, if the S1 peak is outside of a −50 ms to +100 ms time window (or −5% to +10% of the average R-wave period) from the R-wave peak, system 10 may mark S1 sound as indeterminate. In other words, system 10 may indicate that the S1 heart sound for the composite PCG could not be identified because the first detected peak occurs outside the prescribed time window. The failure or inability to detect an S1 heart sound may occur due to the physiology of the patient or an error in detecting the acoustic signal. Similarly, system 10 may validate the S2 peak within a +300 ms to +500 ms time window, with respect to the R-wave peak or trigger. For example, system 10 may notify the user to re-collect electrical and acoustical signals from the patient when the S1 heart sound is indeterminate.

System 10 may then continue traversing the differentiated composite PCG to search for a value less than the low S1 trigger percentage. This value may indicate the end point (e.g., release points) of the S1 heart sound. System 10 may continue to search the differentiated composite PCG for the first point that exceeds the S2 trigger point. The differentiated composite PCG will continue to be searched for a zero crossing point that represents the S2 heart sound peak. System 10 may then validate the identified S2 peak within a prescribed time window (e.g., 300 ms to 500 ms after the R-wave peak).

Using the above algorithm, system 10 may analyze composite PCG 176 and identify related features. PCG value 178 may represent the power of the sound signal. Envelope 180 may be identified as the S1 heart sound and envelope 182 as the S2 heart sound. Composite PCG 176 may be presented as overlaid and time synchronized with ECG 184, which includes R-wave 186 and T-wave 188.

Figure 17:
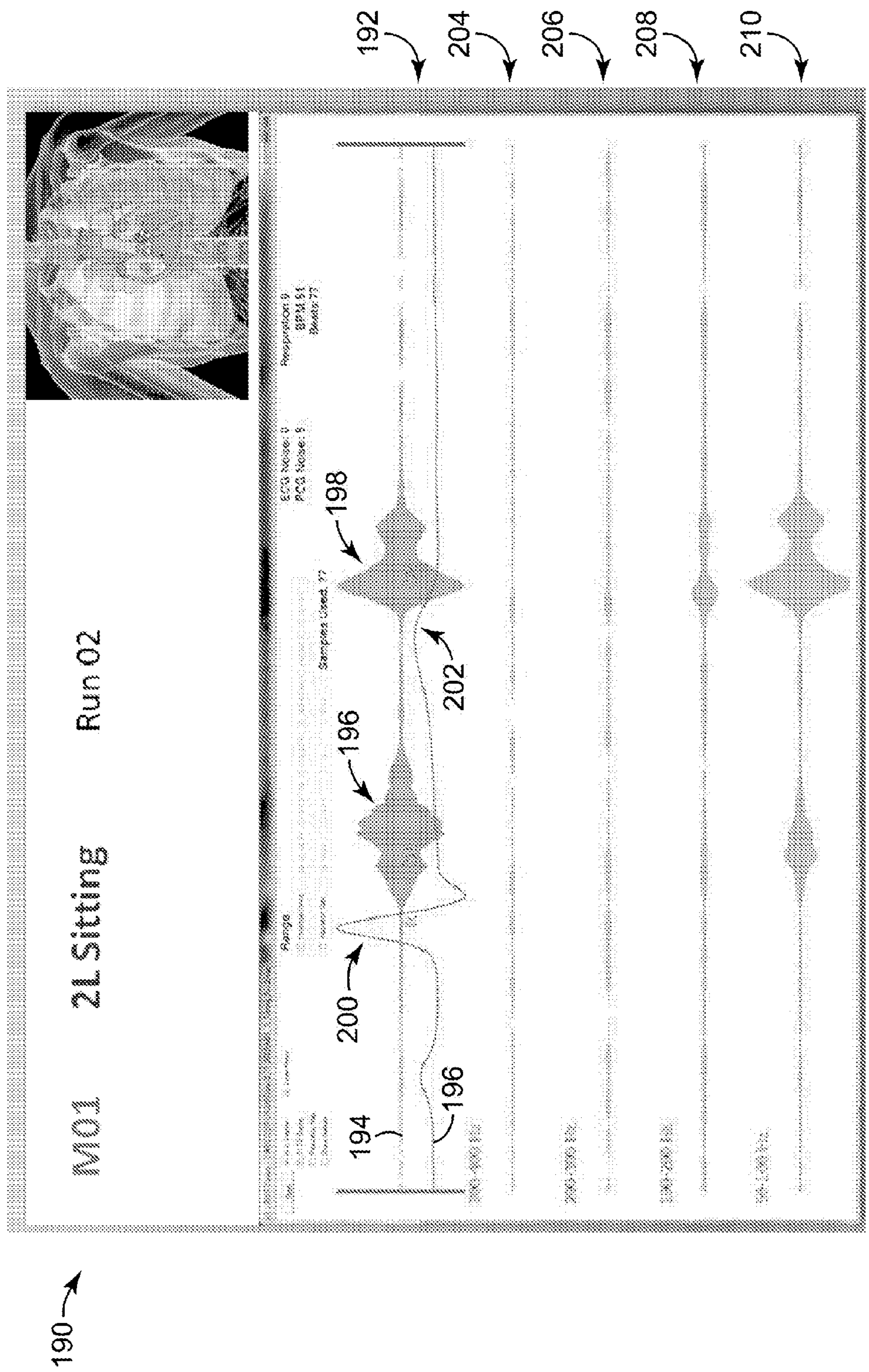
FIGS. 17 and 18 are graphs illustrating example composite PCGs and associated frequency bands for acoustic signals detected at different locations on a patient.
Figure 18:
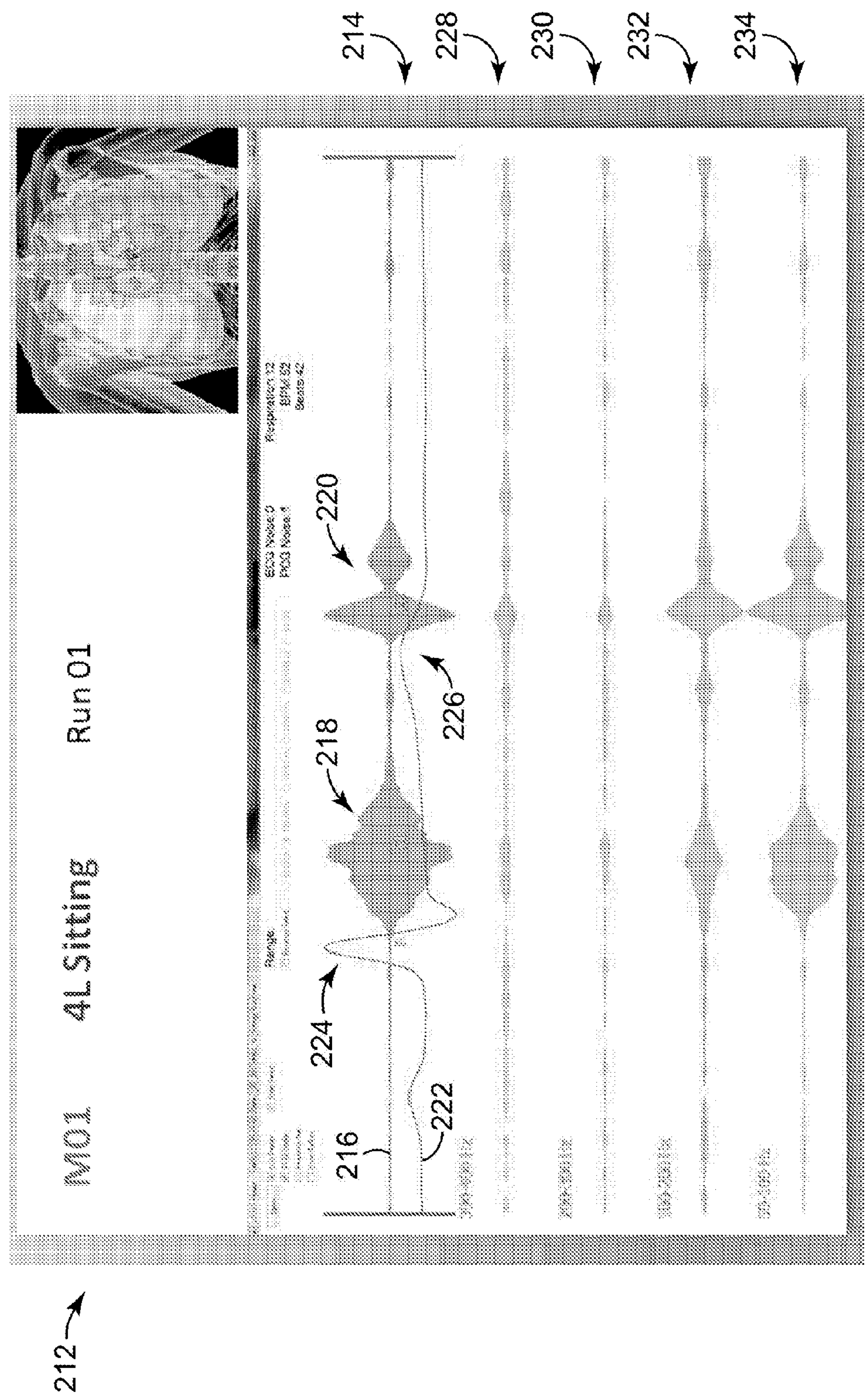

FIGS. 17 and 18 include graphical displays 190 and 212 illustrating example composite PCGs and associated frequency bands for acoustic signals detected at different locations on a patient. As shown in FIG. 17, display 190 may include composite PCG 192. Composite PCG 192 may include PCG value 194 (e.g., a trace of the composite power signal from the filtered acoustic signal), S1 envelope 196 and S2 envelope 198 identified accordingly. Display 190 may further indicate the location of sensor 12 and the orientation of the subject 11 during acquisition of the acoustic signals used in generating composite PCG 192. As depicted, the display 190 indicates that composite PCG 192 was generated from acoustic signals detected at the 2L location when the patient was sitting down. ECG signal 196 is provided with R-wave 200 and T-wave 202 evident.

Display 190 may also include additional features extracted from the acoustic signal based on the selected frequency. For example, frequency bands 204, 206, 208, and 210 may each be composite PCGs generated from the acoustic signal filtered at the respective frequency bands. These frequency bands may include 300-400 Hz, 200-300 Hz, 100-200 Hz, and 50-100 Hz. Frequency band 210 indicates that most of envelopes 196 and 198 are created in the 50-100 Hz frequency band.

System 10 may extract the frequency bands using a variety of techniques. In one example, system 10 may filter the detected acoustic signals using discrete band pass filters. System 10 may then synchronize the acoustic signals to a trigger for each discrete frequency band against the R-wave peak list. System 10 may then perform a RMS power calculation on the resulting signal and then display the RMS signals versus time as indicated in FIG. 17.

Each envelope (e.g., a sound within the cardiac cycle) may be presented to represent a classical form of heart sounds. Instead of providing only a graph of positive amplitude for each envelope, the system may mirror the positive amplitude of each sound to create an envelope with structure above and below the axis of the PCG.

Display 212 may be similar to display 190. Display 212 may include composite PCG 214. Composite PCG 214 may include PCG value 216, S1 envelope 218 and S2 envelope 220 identified accordingly. Composite PCG 214 is depicted as generated from acoustic signals detected at the 4L location when the patient was sitting down (e.g., "4L Sitting"). ECG signal 222 is provided with R-wave 224 and T-wave 226 evident. Graph 212 may also include additional features extracted based on frequency of composite PCG 214. For example, frequency bands 228, 230, 232, and 234 may be provided.

Figure 20:
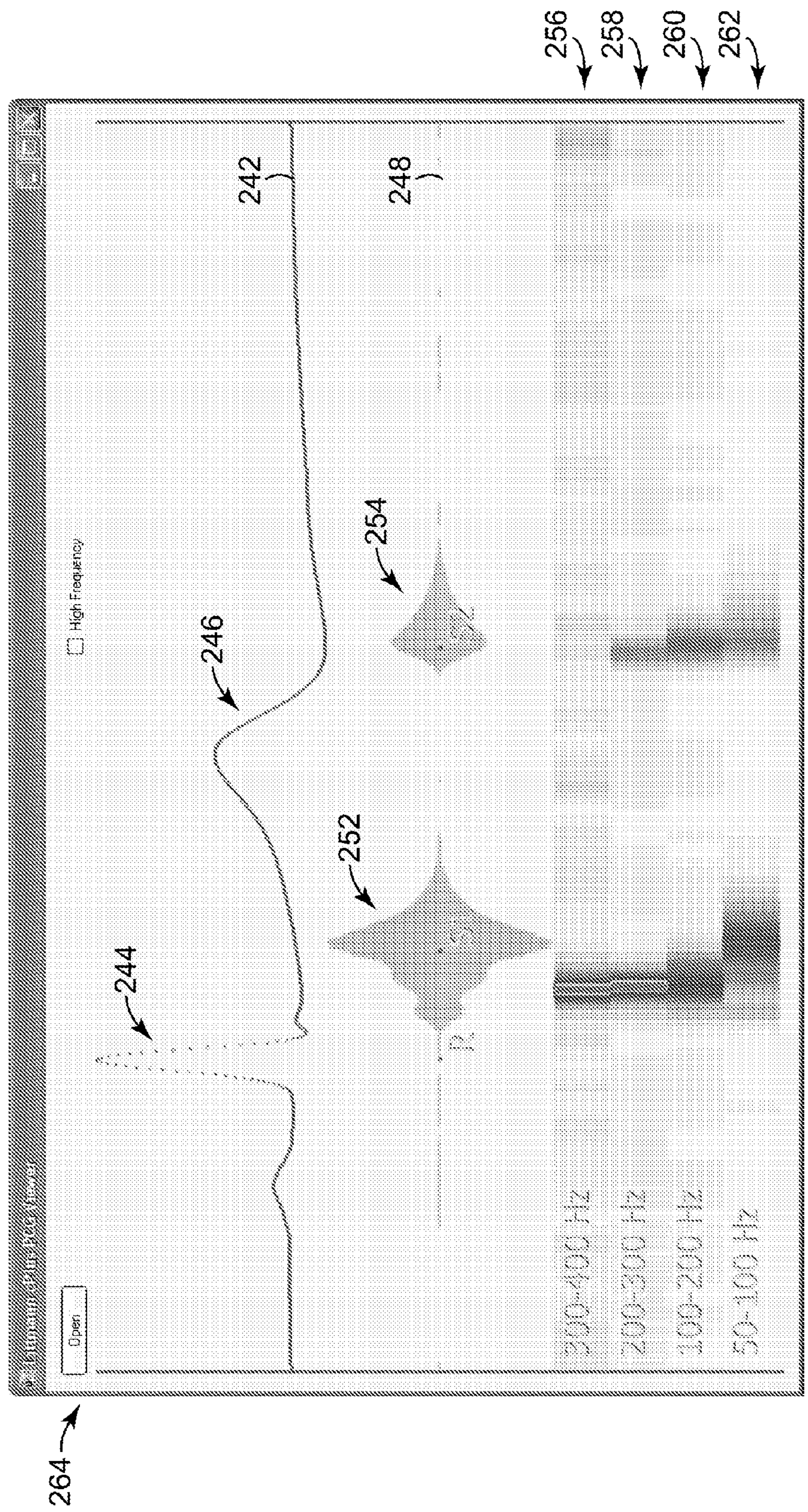
Figure 21:
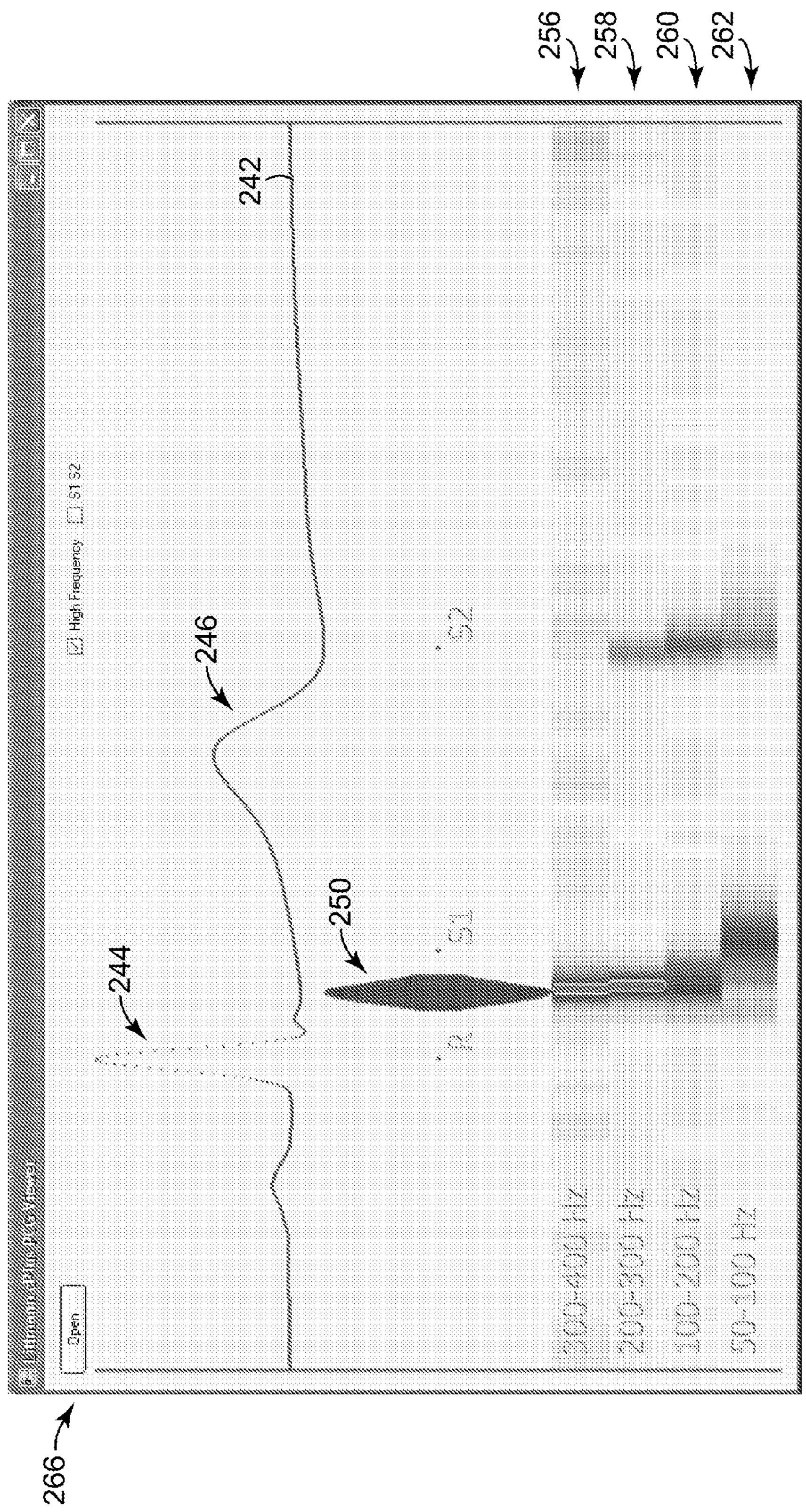

FIGS. 119, 20 and 21 illustrate an exemplary composite PCG 248 with normal and abnormal heart sounds identified within composite PCG 248. System 10 may present composite PCG 248, and other composite PCGs, with abnormal heart sounds identified for the user. The user may then view and/or listen to desired heart sounds of composite PCG 248 together or isolated. This separation may help the user to identify the different pathologies possible using auscultation.

As shown in display 240, composite PCG 248 may include normal heart sounds S1 of envelope 252 and S2 of envelope 254 and abnormal heart sound of envelope 250. Abnormal heart sound of envelope 250 may be presented as a different color than envelopes 252 and 254 or otherwise identified to allow recognition of the abnormality of the heart sound. ECG 242 may also be provided with R-wave 244 and T-wave 246 identified. ECG 242 may also be used to present additional clinical information to patient 11. In addition, frequency bands 256, 258, 260, and 262 may be presented to indicate the frequencies of each envelope 250, 252 and 254, as well as specifically identify any abnormalities.

Display 264 of FIG. 20 shows only envelopes 252 and 254 of normal heart sounds S1 and S2. Envelope 250 of the abnormal sound has been removed. Conversely, display 266 of FIG. 21 shows only envelope 250 of the abnormal heart sound. In addition to visually isolating each heart sound, system 10 may generate an audible representation of composite PCG 248 with all, or only selected, heart sounds present in the composite PCG. This isolation may help the clinician to diagnose the patient and learn the characteristics of certain pathologies present from heart sounds.

Figure 19:
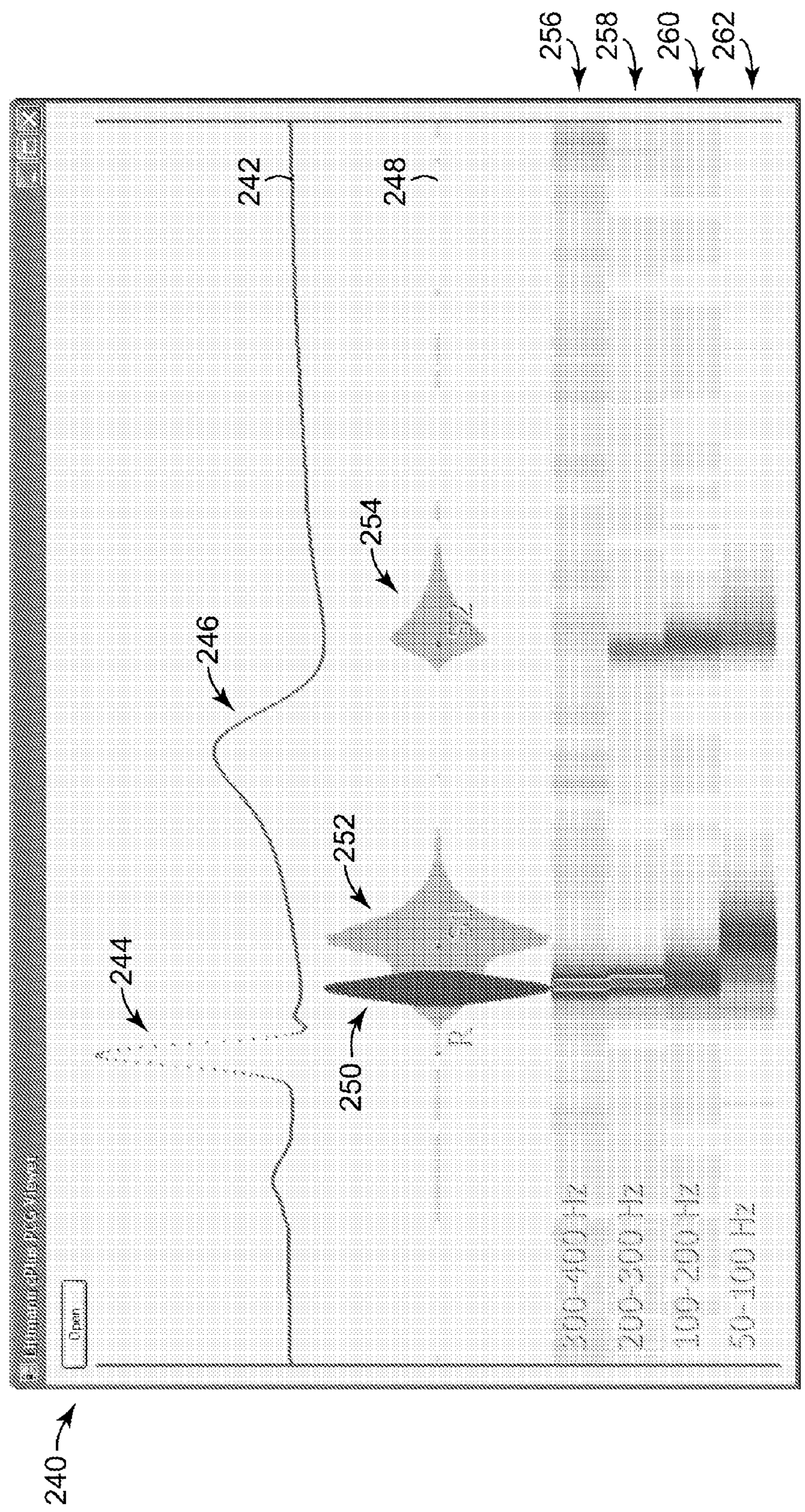
FIGS. 19, 20 and 21 are graphs illustrating an example composite PCG with normal and abnormal heart sounds identified within the composite PCG.
Figure 22:
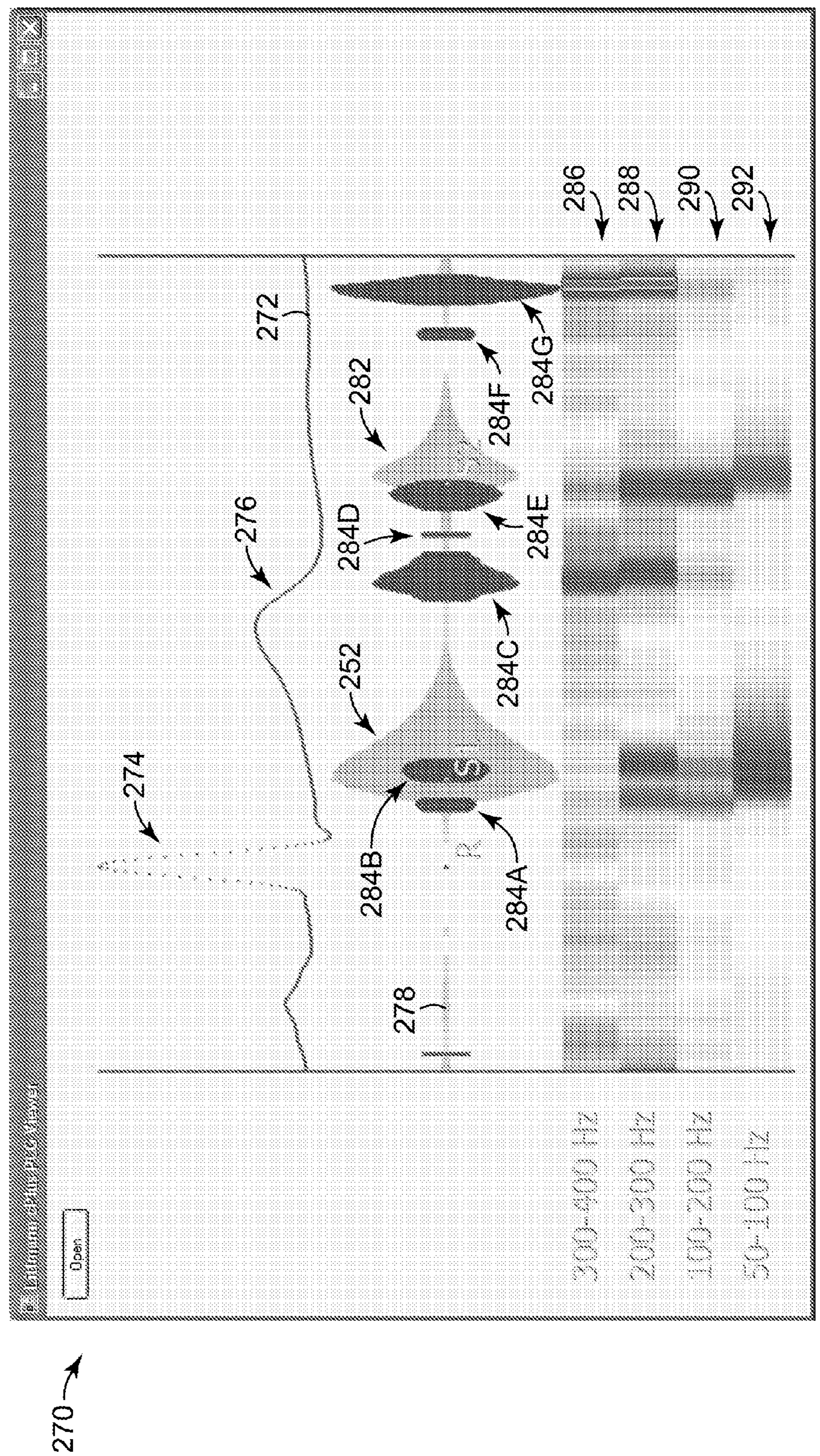
FIG. 22 is a graph illustrating an example composite PCG identifying multiple different heart sounds of an example pathology.

FIG. 22 includes display 270 illustrating an example presentation of composite PCG 278 identifying multiple different heart sounds of an exemplary pathology. Display 270 may be similar to display 240 of FIG. 19. However, display 270 presents a different pathology with multiple heart sounds in addition to normal S1 and S2 sounds. Display 270 includes ECG 272 with R-wave 274 and T-wave 276 for timing perspective within the cardiac cycle. Display 270 also includes composite PCG 278 that includes envelopes 280 and 282 of normal S1 and S2 heart sounds. Envelopes 284A, 284B, 284C, 284D, 284E, 284F, and 284 G are each separate heart sounds representative of at least one pathology. These sounds may be difficult to identify audibly and in real-time. However, visual representation of the sounds may allow for identification of the heart sounds and diagnosis of the patient. Frequency bands 286, 288, 290, and 292 may also be presented to identify the frequencies of each envelope.

Figure 23:
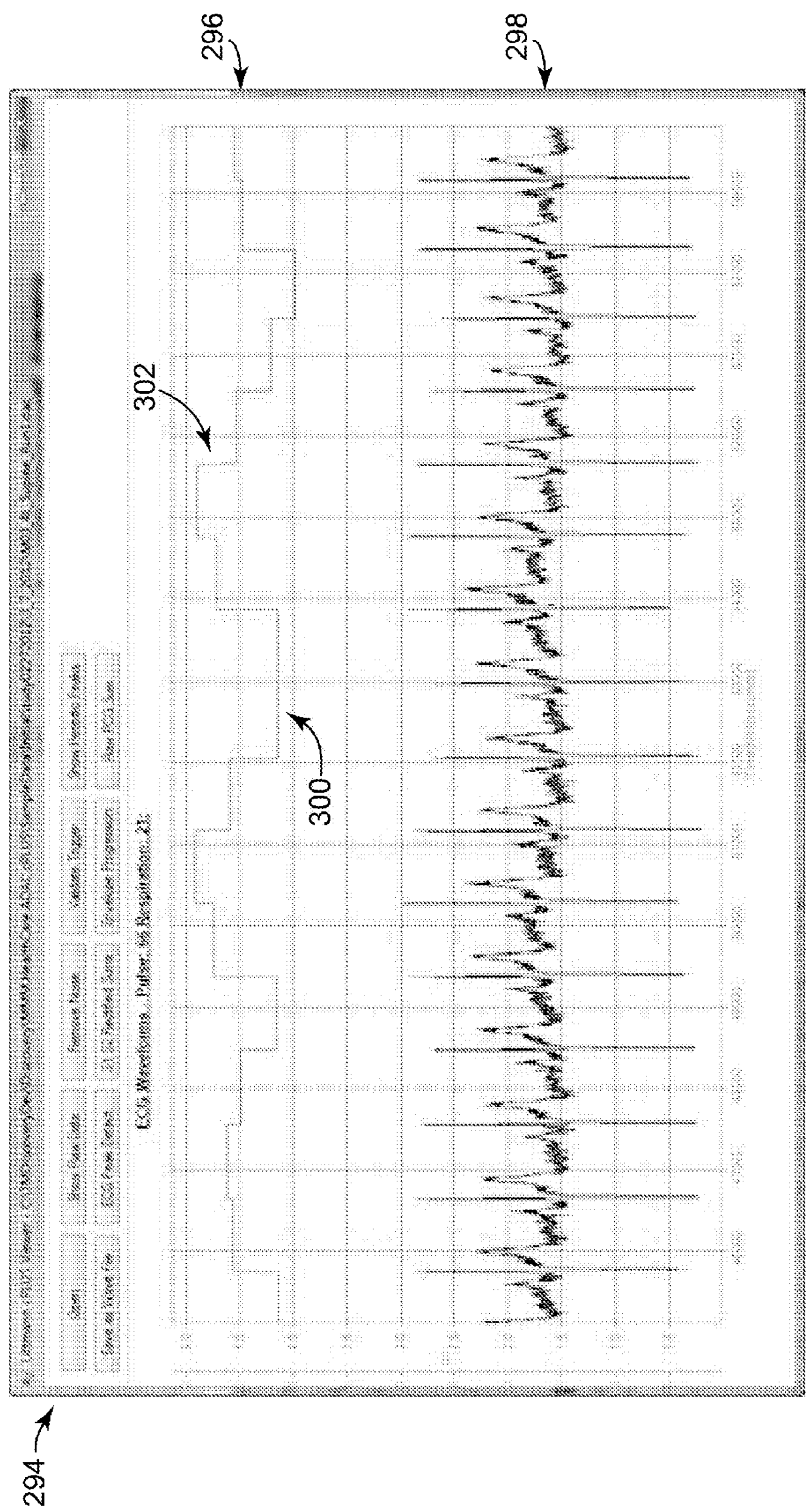
FIGS. 23 and 24 are graphs illustrating breathing phases identified from an example electrocardiogram.
Figure 24:
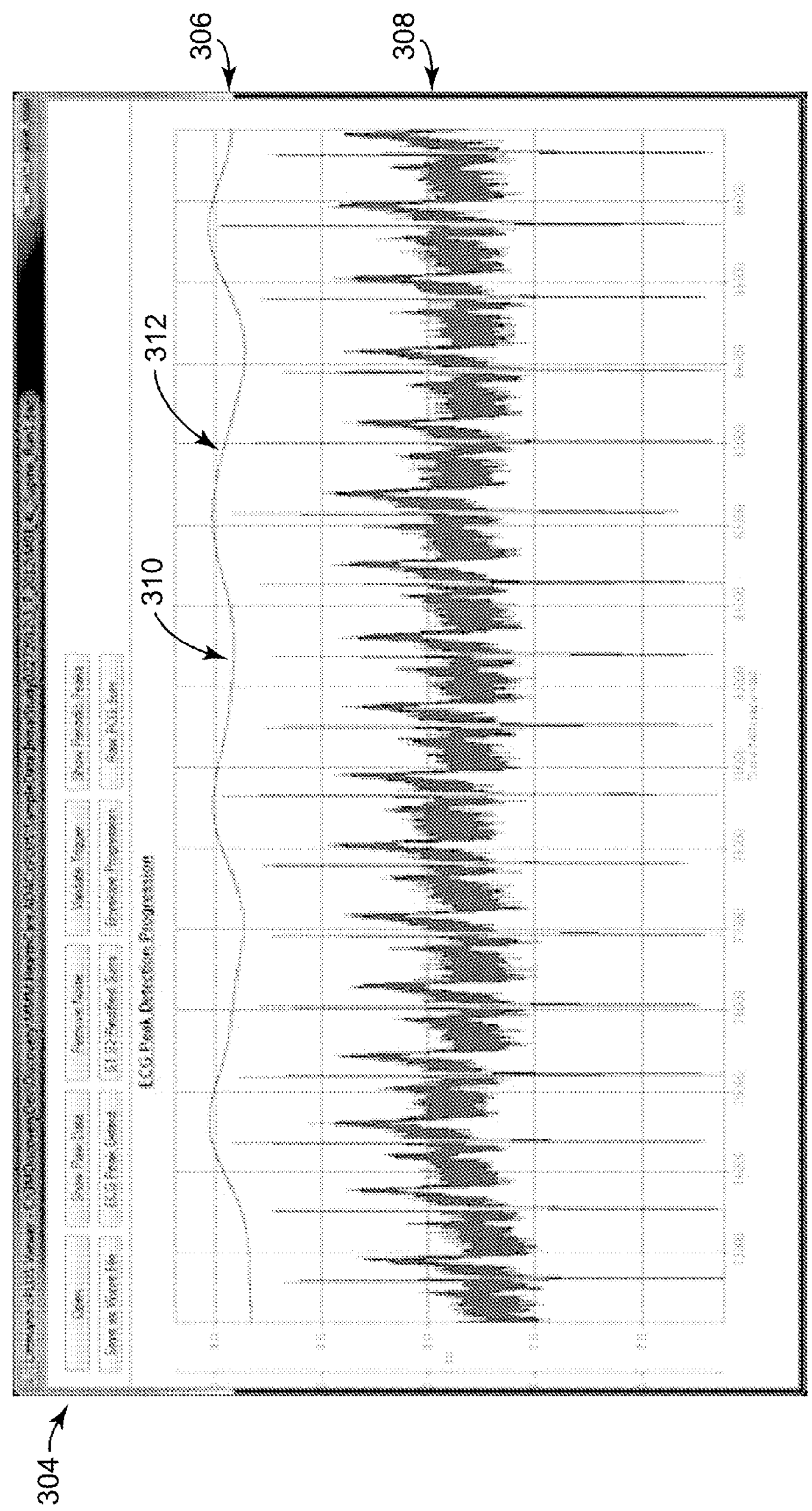

The system 10 can, in certain implementations, analyze an ECG signal to identify two or more phases of the breathing cycle that may affect detected acoustic signals. The breathing phases may then be used to sort the acoustic signals and present a composite PCG specific to each breathing phase. FIGS. 23 and 24 are graphs illustrating breathing phases identified from of an example electrocardiogram. As shown in FIGS. 23 and 24, ECG 298 and ECG 308 fluctuate in magnitude based on the breathing of the patient. ECG 298 may be analyzed to identify two or more phases of the breathing cycle that may affect detected acoustic signals. Breathing trace 296 may be a step graph showing the change in R-wave height from ECG 298 that reflects respiration of the patient.

As described above with respect to FIG. 13, system 10 may calculate peaks and valleys in the R-wave peak list. System 10 may build the step graph of breathing trace 296 by plotting the magnitude of R-waves versus time. System 10 may also smooth the step graph using a low-pass filter and differentiate the resulting signal of breathing trace 296. Breathing trace 296 may include peaks 302 to reflect peak inspiration and valleys 300 to reflect the bottom of expiration. Alternatively, system 10 may build a spline graph (e.g., a linear spline or polynomial spline fit) shown as breathing trace 306 of FIG. 23 or any other best-fit curve. Breathing trace 306 of graph 304 may include peaks 312 for the top of inspirations and valleys 310 for the bottom of expirations. Breathing trace 306 may be generated from ECG 308.

System 10 may determine the features or phases of breathing to later sort respective acoustic signals and generate an associated composite PCG for each breathing phase. System 10 may augment the R-wave peak list with one or more breathing properties. For example, system 10 may traverse the differentiated step signal generated from the ECG and locate one or more features such as positive slope areas, peaks, negative slope areas, and minimums. An "inspiration" property may be added to the R-wave list entries corresponding to positive sloped areas of the step graph. A "top of inspiration" property may be added to the R-wave list entries corresponding to the positive peaks in the step graph. An "expiration" property may be added to the R-wave list entries corresponding to the negative sloped areas of the step graph. And, a "bottom of expiration" property may be added to the R-wave list entries corresponding to the negative peaks in the step graph. In other examples, more or fewer phases of breathing may be identified to generate composite PCGs desired by the user or necessary to diagnose the patient.

Figure 25:
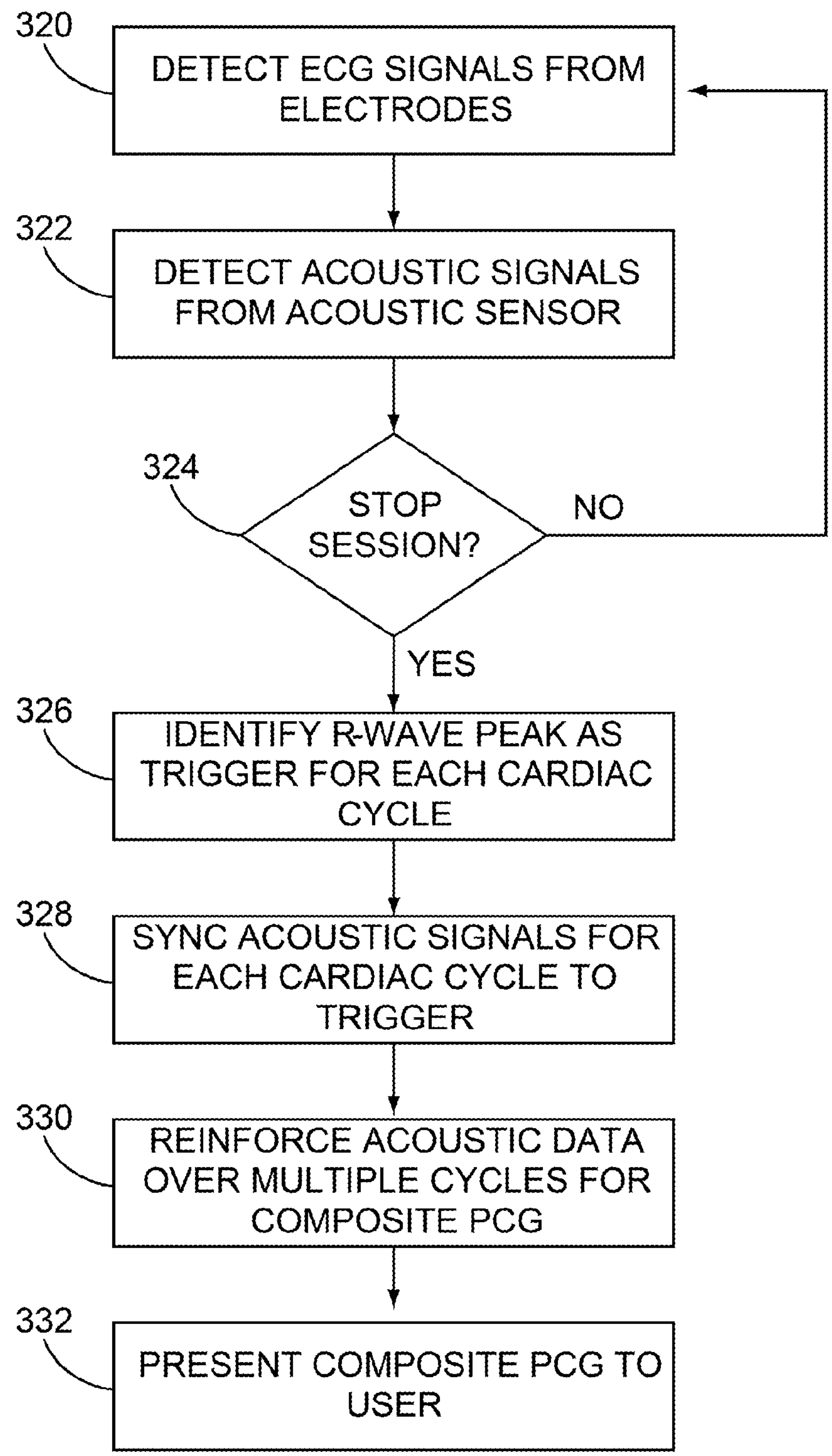
FIG. 25 is a flow diagram illustrating an example process for detecting electrical and acoustic signals and generating a composite PCG.
Figure 26:
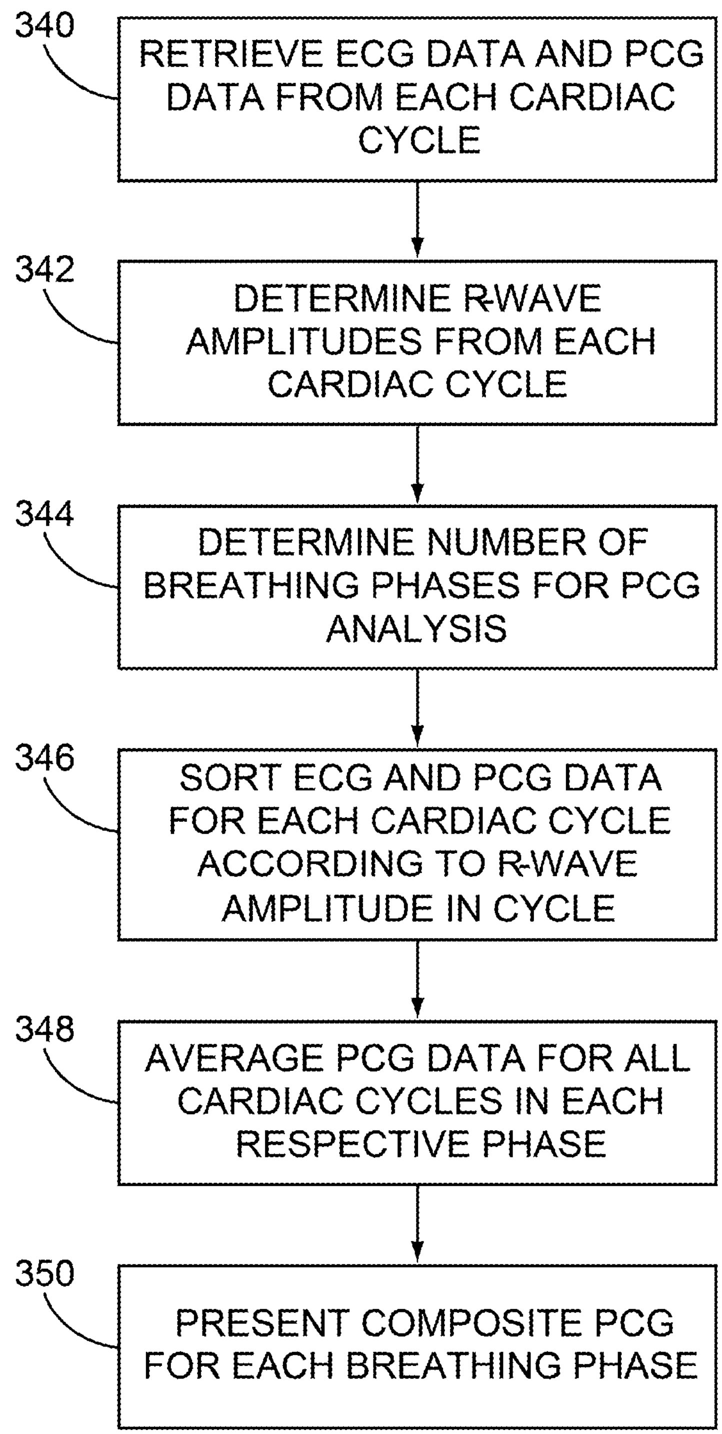
FIG. 26 is a flow diagram illustrating an example process for generating composite PCGs for different phases of breathing.
Figure 27:
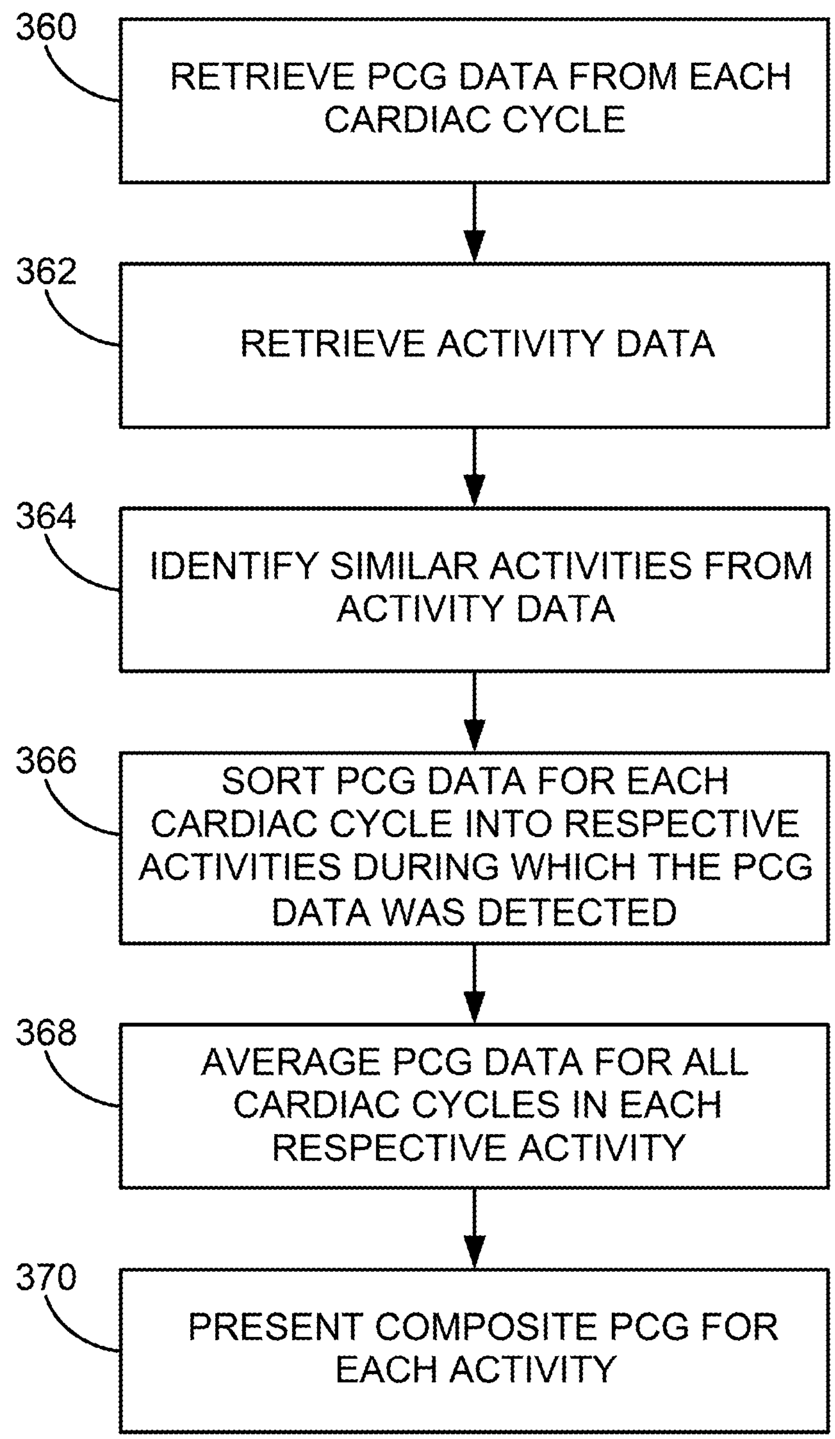
FIG. 27 is a flow diagram illustrating an example process for generating composite PCGs for different activities of the patient.

FIGS. 25, 26, and 27 include example processes than may be performed that are related to auscultation and cardiac sounds described herein. Detection device 12 (e.g., processor 70) and computing device 18 will generally be described as performed each of these processes. However, in other examples, the processes of FIGS. 25, 26, and/or 27 may be fully or at least partially performed by wireless headset 36, remote server 104, or remote device 108. Each of these devices or systems may individually perform each step or the tasks may be distributed over two or more devices.

FIG. 25 is a flow diagram illustrating an example process for detecting electrical and acoustic signals and generating a composite PCG. As shown in FIG. 25, sensing module 86 may detect electrical signals (e.g., ECG signals) from two or more electrodes coupled to detection device 12 (320). Detection device 12 may also detect acoustic signals from acoustic sensor 84 (322). If the detection session is not to stop or detection device 12 requires more data ("NO" branch of block 324), detection device 12 may continue to detect ECG and acoustic signals (320).

If the detection session is complete ("YES" branch of block 324), processor 70 may analyze the electrical signals and acoustic signals for generating a composite PCG. Processor 70 may identify R-wave peaks as the trigger for each cardiac cycle (326). Processor 70 may then synchronize the acoustic signals for each cardiac cycle to the identified trigger (328). Processor 70 may then reinforce the acoustic data over multiple cardiac cycles to generate the composite PCG (330). In other words, the acoustic signals may be averaged or summed to reinforce actual heart sounds present in the acoustic signals and reduce or eliminate the presence of noise or non-heart sounds in the acoustic signals. Detection device 12 and/or computing device 18 may then present the composite PCG to a user (332). The composite PCG may be presented via visual or audio means.

FIG. 26 is a flow diagram illustrating an example process for generating composite PCGs for different phases of breathing. Processor 70 may retrieve ECG data (e.g., electrical signals) and PCG data (e.g., acoustic signals) from each cardiac cycle (340). Processor 70 may determine the R-wave amplitudes from each cardiac cycle (342) and determine the number or type of breathing phases for the PCG analysis (344). Example breathing phases may include inspiration, expiration, the peak of inspiration, and the bottom of expiration.

Processor 70 may sort the ECG data and the PCG data for each cardiac cycle according to the R-wave amplitude of the respective cycles (346). For each breathing phase, processor 70 may then average the respective, or sorted, PCG data for all cardiac cycles (348). Processor 70 may then generate a composite PCG for each of the breathing phases and present the composite PCGs to the user (350). In some examples, detection device 12 may transmit the composite PCGs to computing device 18 for presentation to the user.

FIG. 27 is a flow diagram illustrating an example process for generating composite PCGs for different activities of the patient. Processor 70 may retrieve PCG data (e.g., acoustic signals) from each cardiac cycle (360). Processor 70 may also retrieve activity data from activity sensor 82 (362). Processor 70 may analyze the activity data to identify similar activities and/or predefined activities from the activity data (364). For example, the predefined activities may include sitting, standing, walking, lying down, or any other maneuvers that may isolate one or more potential heart sound pathologies.

Processor 70 may then sort the PCG data for each cardiac cycle into respective activities during which the PCG data was detected (366). In other words, the PCG data may be associated with the activities the patient was engaged in when the PCG data was detected. For each activity, processor 70 may then average the respective, or sorted, PCG data for all cardiac cycles (368). Processor 70 may then generate a composite PCG for each of the activities and present the composite PCGs to the user (370). In some examples, detection device 12 may transmit the composite PCGs to computing device 18 for presentation to the user.

In one embodiment, the patient may be instructed by an automated testing system to run through a series of maneuvers designed to enhance the physiological conditions to reveal underlying heart pathologies. For example, the automated testing system may instruct the patient to transition from a sitting position to a standing position, breathe deeply, or squeeze a ball. The instructions to the patient can be automatically provided by a GUI interface or guided by a clinician. The automated testing system senses whether the patient is complying with the instructions (e.g. movement sensing by accelerometer, breathing by ECG variation) and verifies the intensity of the maneuver. If needed, the automated testing system may request that the patient repeat maneuvers if they are not adequately performed or if the data is not properly collected.

Figure 28:
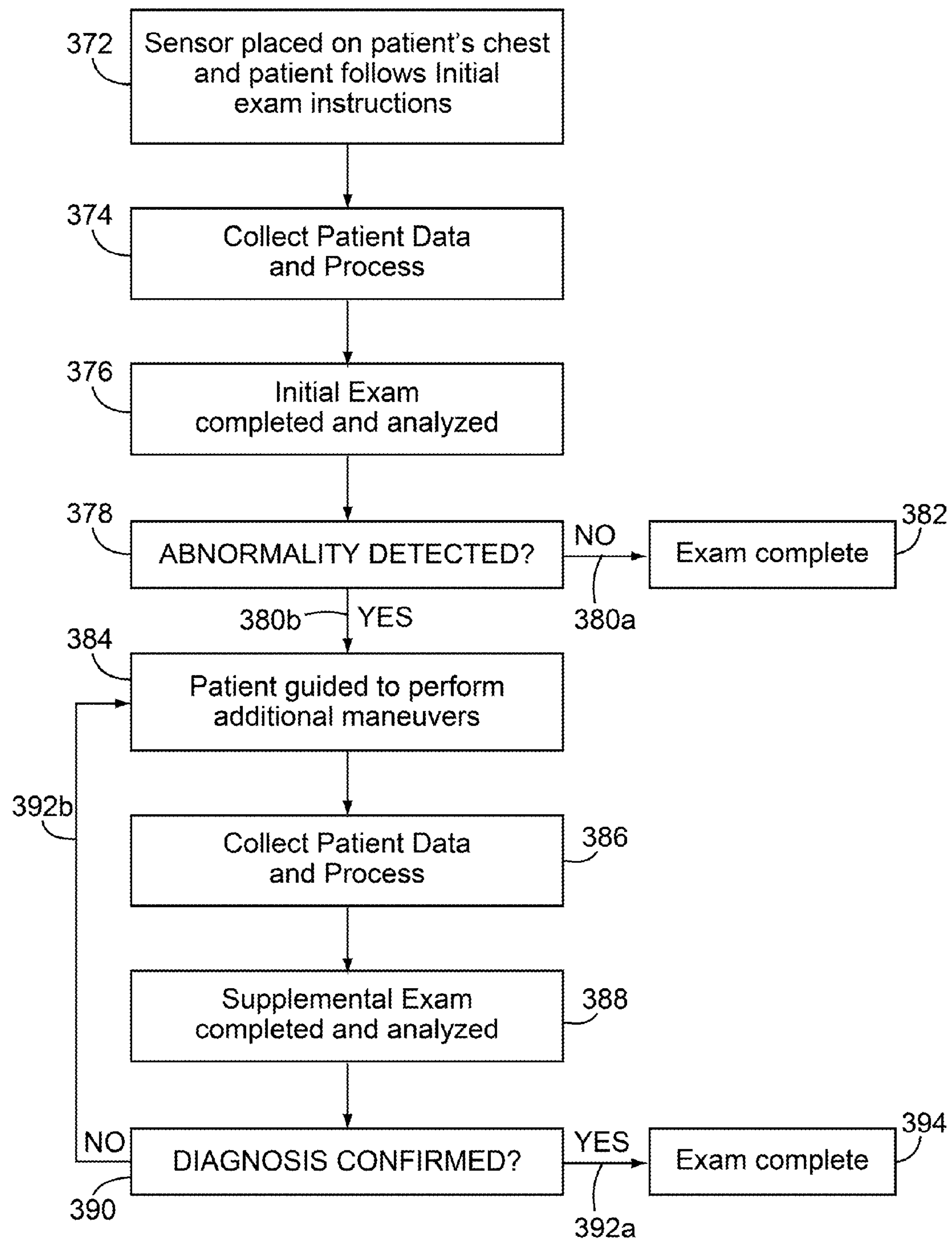
FIG. 28 is a flow diagram illustrating an example process for patient examination with an interactive graphical user interface.

FIG. 28 shows a flow diagram of a computer guided examination of a patient. As a first step, after sensor(s) are placed on the patient's chest, the patient goes through initial examination instructions (372). The patient data is then collected and processed (374) and the initial examination is completed and analyzed (376). If there are no abnormalities detected (378 and 380*a*), the examination is complete (382). If an abnormality is detected (378 and 380*b*), the patient is then guided to perform additional maneuvers (384). The data is then collected and processed (386) and the supplemental examination is completed and analyzed (388). If the diagnosis is confirmed, (390 and 392*a*), then the examination is complete (394). If the diagnosis is not confirmed (390 and 392*b*), then the patient may be asked to perform additional maneuvers (384). The additional data is collected and processed and the supplemental examination is again completed and analyzed. This process may be repeated.

Figure 29:
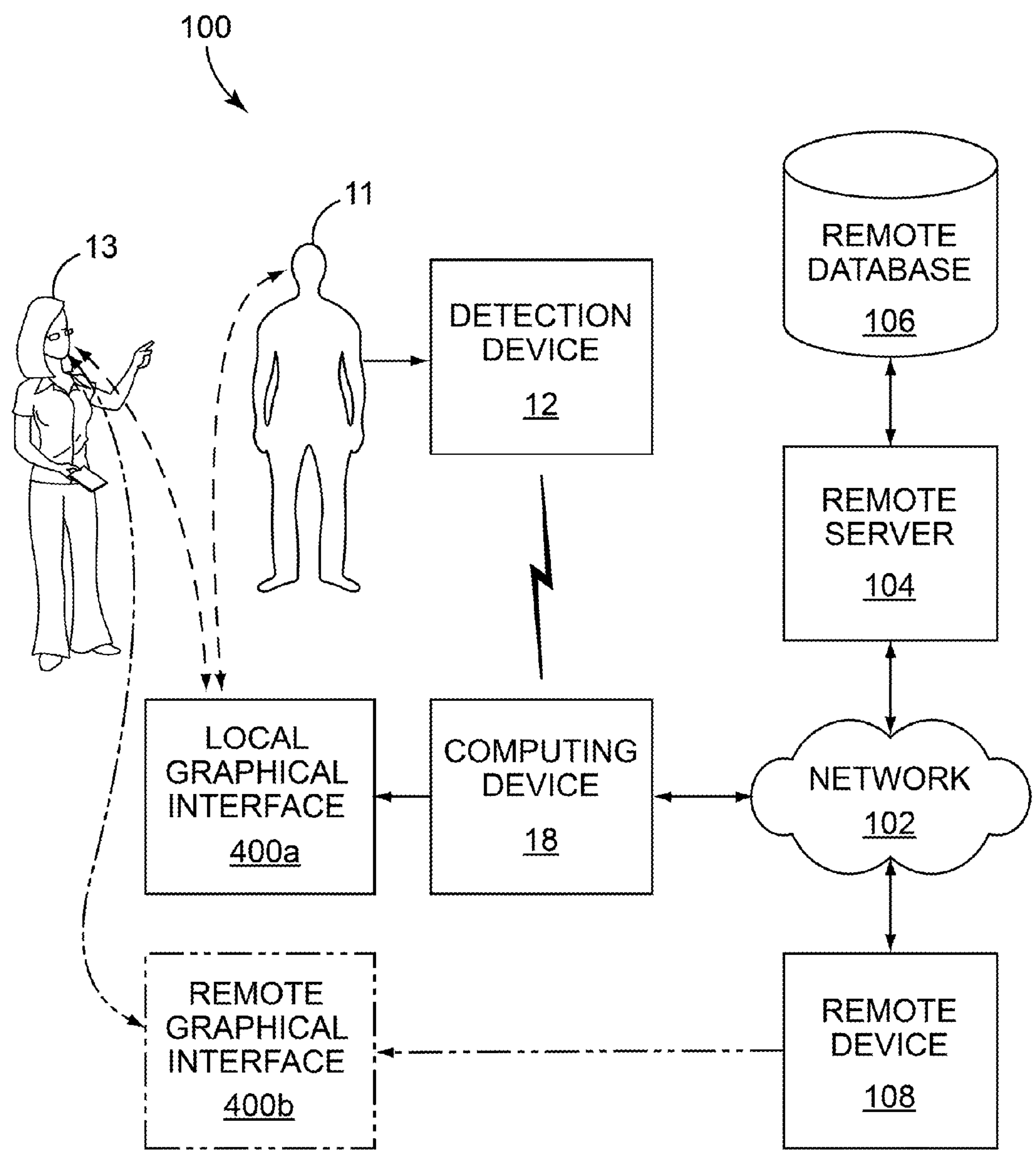
FIG. 29 is a conceptual diagram illustrating an example system for patient examination with an interactive graphical user interface.

FIG. 29 is a conceptual diagram illustrating using system 100 to guide patient 11 through a series of maneuvers. System 100 works as discussed in FIG. 9 except that computing device 18 is also connected to at least one of local graphical interface 400*a* and remote graphical interface 400*b*, where computing device 18 is connected to remote graphical user interface via network 102 and remote device 108. In one embodiment, system 100 communicates directly with patient 11 such that the process is self-directed. In this case, patient 11 may receive instructions via local graphical interface 400*a*.

In another embodiment, system 100 communicates with patient 11 via a health care provider 13, for example, through a clinician, nurse, or doctor. Health care provider 13 may communicate with patient 11 orally or via local graphical interface 400*a*, remote graphical interface 400*b* or through other telecommunication means, such as a telephone. For example, if patient 11 is using system 100 from his/her home, patient 11 may be taking instructions via telephone. If patient 11 is using system 100 at a clinic or hospital, patient 11 may be taking instructions via local graphical interface 400*a* or directly from health care provider 13. For example, when health care provider 13 is at the same location as patient 11, health care provider 13 may use the prompts on local graphical interface 400*a* to guide patient 11 in performing a series of maneuvers. When health care provider 13 is located remotely from patient 11, health care provider 13 may refer to the prompts on remote graphical interface 400*b* to guide patient 11 in performing a series of maneuvers. Thus, although FIG. 29 depicts health care provider 13 as being located proximate patient 11, system 100 is also designed such that health care provider 13 may be in a remote location.

In yet another embodiment, more than one health care provider may be involved in directing patient 11 through the series of maneuvers. For example, a nurse may be (local) in an examination room with patient 11 and providing instructions on what series of maneuvers to perform. The data collected may then be sent to a doctor in a remote location. After reviewing the data, the doctor may subsequently send instructions through remote device 108 back to the nurse through local graphical interface 400*a* or remote graphical interface 400*b* to guide patient 11 through additional maneuvers. In this embodiment, the interaction of the doctor at the remote location with the nurse and patient may occur in real time or in a "store and send data" session.

As mentioned above in the discussion of FIG. 3, in some instances it may be beneficial to include more than one sensor or detection device in the system. In one embodiment, the automated testing system could instruct the patient (or tell the clinician) to attach additional sensors, such as electrical sensors or acoustic sensors, and direct the patient (or clinician) via the GUI as to where to place the additional sensors. There could also be a check to verify that the sensors have been correctly placed. If the sensors were not correctly placed, the processor 70 could guide the patient to properly position the sensors.

Once the patient has completed all of the maneuvers, the examination can be sequentially refined and/or enhanced based on the results. In one embodiment, remote database 106 may store historical or previous composite PCGs generated for patient 11. Remote server 104 may then identify any changes and relay such past patient data back to computing device 18 and/or remote device 108, with such communications occurring in real-time in the presence of patient 11 via a detection device or offline by remote access.

Figure 30:
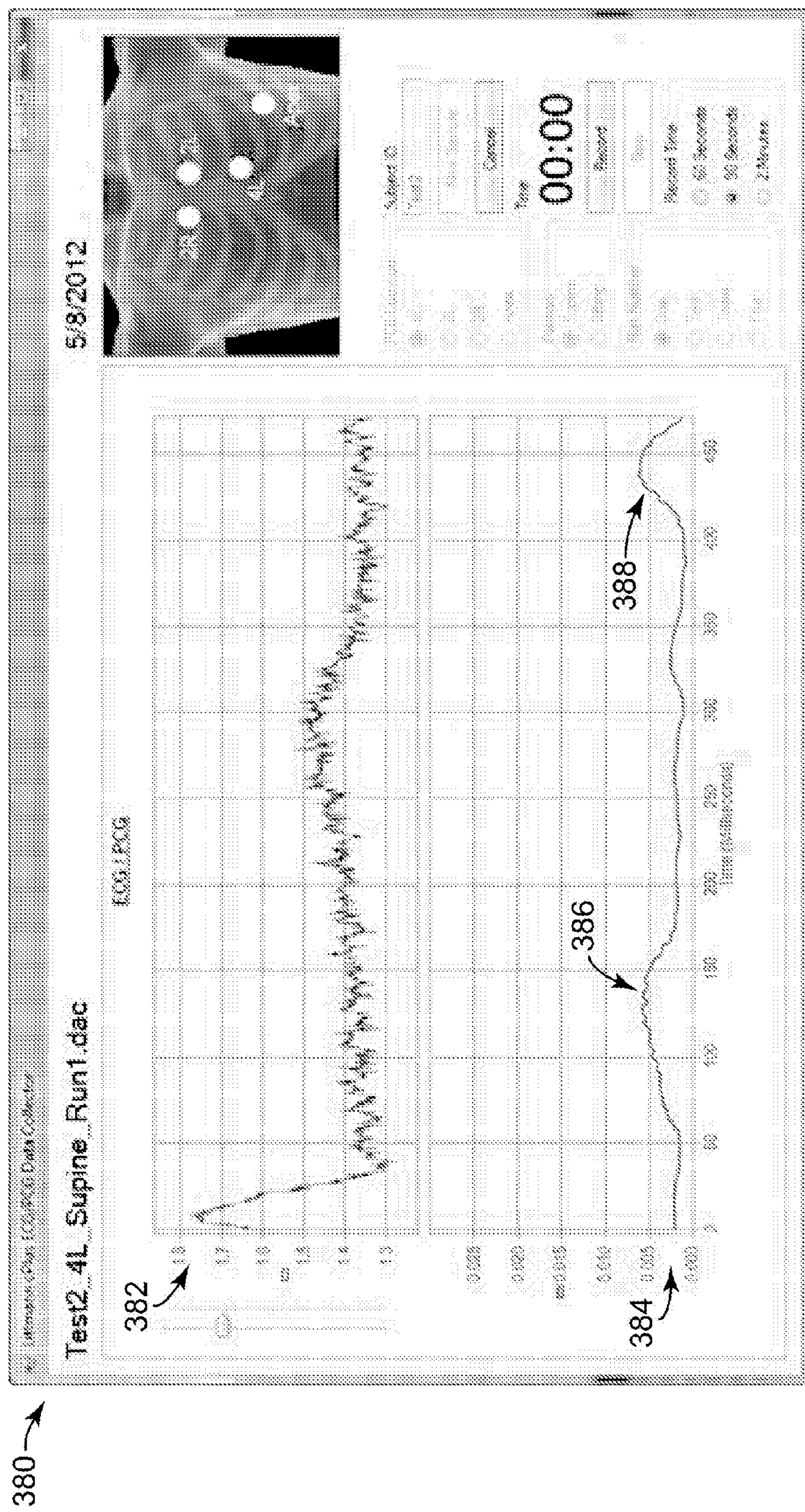
FIGS. 30 and 31 are graphs illustrating real-time electrical signals and acoustic signals displayed to facilitate positioning a detection device on a patient.
Figure 31:
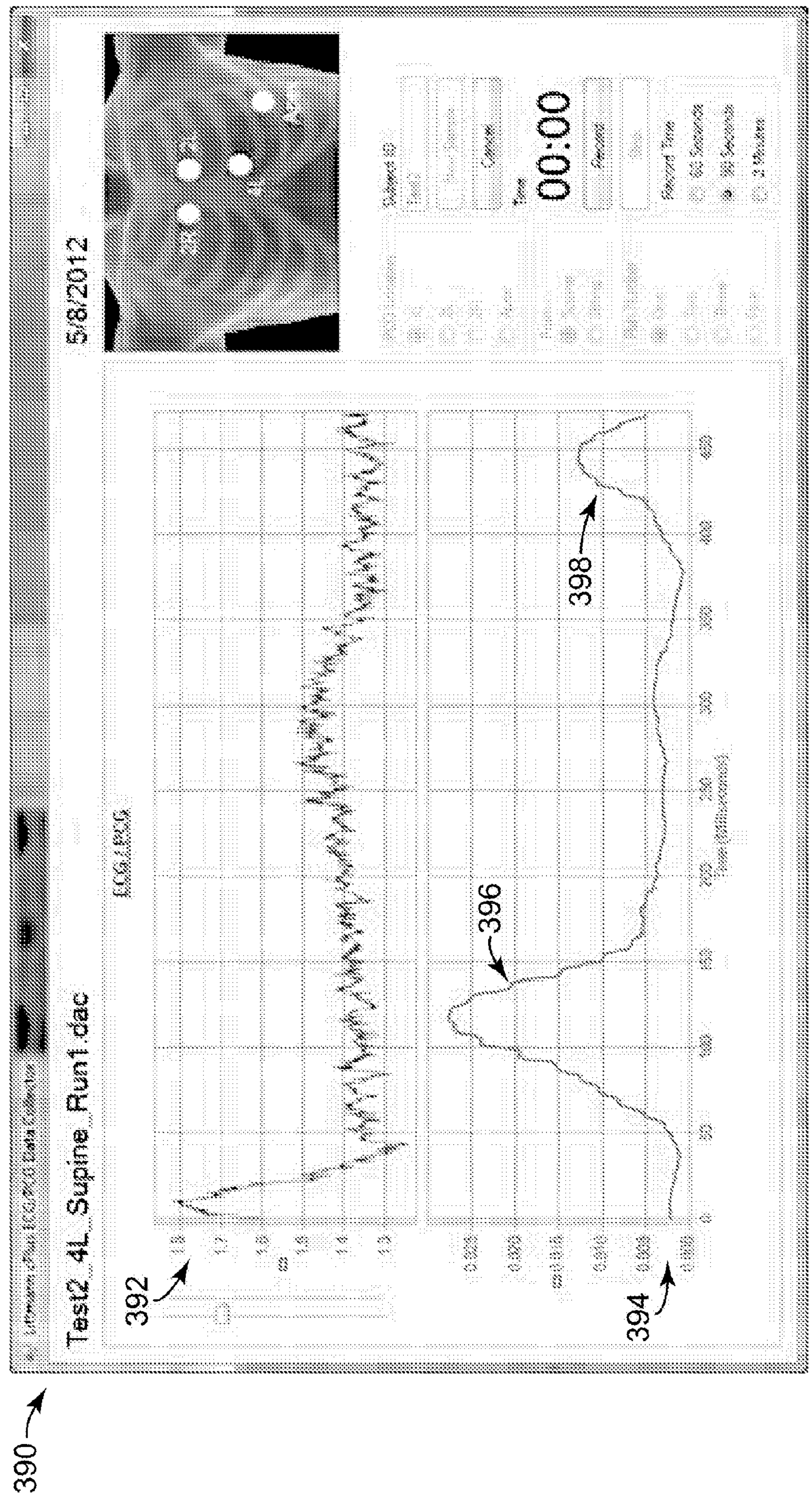

FIGS. 30 and 31 are illustrate real-time electrical signals and acoustic signals displayed to facilitate positioning detection device 12, or any other detection device described herein, on a patient. PCG 384 of FIG. 30 and PCG 394 of FIG. 31 are example phonocardiograms generated in real-time, or as the user is moving detection device 12 with respect to the patient. ECG 382 and 392 may identify the R-wave of the cardiac cycle to allow the user to identify the desired S1 and S2 sounds.

If the user has not positioned the acoustic sensor of detection device 12 appropriately over an intercostals space such that the detected acoustic signal is weak, PCG 384 may indicate to the user that detection device 12 should be moved. PCG 384 includes a small feature 386 for the S1 heart sound and a small feature 388 for the S2 heart sound. Conversely, PCG 394 of FIG. 31 indicates that detection device 12 is positioned appropriately on the patient. PCG 394 includes relatively large feature 396 for the S1 heart sound and relatively large feature 398 for the S2 heart sound. Since PCGs 384 and 394 may be provided to the user in real-time, the user may continue to move detection device 12 on the chest of the patient until the largest S1 and S2 features, or other desired features, are presented to the user.

In one example, this location technique may be referred to as "auscultation signal quality reporting." Processor 70 of detection device 12 or processor 90 of computing device 18, for example, may use live or real-time band pass filtering and RMS calculations to determine the relative auscultatory quality of the detected acoustic signals. Processor 70 may perform Butterworth band pass filtering between approximately 30 Hz and 400 Hz on the streaming acoustic signal. Processor 70 may also perform RMS calculations on the filtered and streaming acoustic signal. The resulting PCG waveform may then be presented to the user for real-time assessment of the acoustic signal strength from detection device 12.

In some examples, the location technique describe herein may automatically indicate which direction the user should move detection device 12. Detection device 12 may monitor the movement of detection device 12 from activity sensor 82 in addition to the strength of the PCG waveform in real-time. If the strength of the PCG waveform is increasing with movement, detection device 12 may provide an arrow, plus sign, and/or audible sound to indicate that the user should continue moving the detection device in that same direction. Conversely, if the strength of the PCG waveform is decreasing with movement, detection device may provide an arrow, minus sign, and/or audible sound to indicate that the user should move the detection device in a different direction. This directional indication provided by detection device 12 may facilitate locating an effective position with which to detect acoustic signals from the patient.

Although the averaging of acoustic signals is described herein to produce composite PCGs, the same averaging or summing of electrical signals may be used to generate composite ECG signals for a single cardiac cycle. In general, any of the devices described herein may present visual or audio representations of acoustic signals as they are detected (e.g., in real-time) and/or composite PCGs. In some examples, the composite PCG may be presented on top of, or overlaid, with the real-time acoustic signals. This technique may be used to train the clinician to recognize normal sounds or various pathologies. Each of these listening modes may be presented in a desired form, such as with a bell filter or a diaphragm filter.

The techniques described in this disclosure may be implemented, at least in part, in hardware, software, firmware, or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various techniques described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware, firmware, or software components. Rather, functionality associated with one or more modules or units may be performed by separate hardware, firmware, or software components, or integrated within common or separate hardware, firmware, or software components.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, or optical media.

In some examples, a computer-readable storage medium may comprise non-transitory medium. The term "non-transitory" may indicate that the storage medium is not embodied in a carrier wave or a propagated signal. In certain examples, a non-transitory storage medium may store data that can, over time, change (e.g., in RAM or cache).

Various aspects of the disclosure have been described. These and other embodiments are within the scope of the following claims.

What is claimed is:

1. A system comprising:

an acoustic sensor configured to detect an acoustic signal from a heart of a patient;

a sensing module configured to detect an electrical signal from the heart of the patient via two or more electrodes; and at least one processor configured to:

for each cardiac cycle of a plurality of cardiac cycles, identify a trigger point associated with the detected electrical signal, wherein the trigger point is associated with an R-wave of each cardiac cycle of the detected electrical signal;

generate acoustic information from the detected acoustic signal;

synchronize the acoustic information to the trigger point for each cardiac cycle;

generate a phonocardiogram as a composite phonocardiogram based on the synchronized acoustic information, wherein the composite phonocardiogram is generated for a representative cardiac cycle;

determine R-wave amplitudes from each of the plurality of cardiac cycles;

determine a plurality of different breathing phases within a single breathing cycle;

for each cardiac cycle, sort the synchronized acoustic information into one of the different breathing phases; and generate a breathing phase composite phonocardiogram for each of the different breathing phases by averaging the synchronized acoustic information in each of the respective breathing phases.

2. The system of claim 1, wherein the at least one processor is configured to compare the composite phonocardiogram to a plurality of stored pathologies;

determine when at least a portion of the composite phonocardiogram matches one of the plurality of stored pathologies; and discriminate an abnormal portion of the composite phonocardiogram associated with the one stored pathology from a normal portion of the composite phonocardiogram.

3. The system of claim 2, wherein the at least one processor is configured to discriminate the abnormal portion from the normal portion by identifying a first frequency band associated with the abnormal portion and a second frequency band associated with the normal portion.

4. The system of claim 2, wherein the processor is configured to present the identified portion of the composite phonocardiogram to a user.

5. The system of claim 1, further comprising a housing and the two or more electrodes each coupled to a respective wire, wherein a housing comprises the acoustic sensor, the sensing module, the at least one processor, and wherein the sensing module is configured to couple with the respective wires of the two or more electrodes.

6. The system of claim 1, further comprising a housing and the two or more electrodes, wherein the housing comprises the acoustic sensor, the sensing module, the at least one processor, and the two or more electrodes disposed on the housing.

7. The system of claim 1, further comprising an electrode housing comprising the two or more electrodes and a detector housing, wherein the detector housing comprises the acoustic sensor, the sensing module, the at least one processor, and communication module configured to communicate with the electrodes of the electrode housing.

8. The system of claim 1, further comprising a telemetry module configured to communicate with a computing device.

9. The system of claim 1, further comprising a computing device, wherein the computing device comprises a user interface configured to present the phonocardiogram.

10. The system of claim 9, wherein the user interface comprises an audio output configured to present the phonocardiogram audibly to the user.

11. The system of claim 9, wherein the user interface comprises a display configured to present the phonocardiogram visually to the user.

12. The system of claim 1, wherein the at least one processor is configured to generate a waveform based on an acoustic signal and an electrical signal detected over at least one cardiac cycle of the heart, generate a phonocardiogram by mirroring the waveform about an axis of the waveform, and identify at least one heart sound within the phonocardiogram; and a user interface configured to visually present the phonocardiogram and the identification.

13. The system of claim 12, wherein:

the processor is configured to identify the phonocardiogram as at least one pathology; and the user interface is configured to present the at least one pathology with the at least one identified heart sound.

* * * * *